United States Patent [19]

Rizzardo et al.

[11] Patent Number: 5,385,996
[45] Date of Patent: Jan. 31, 1995

[54] CONTROL OF MOLECULAR WEIGHT AND END-GROUP FUNCTIONALITY OF POLYMERS

[75] Inventors: Ezio Rizzardo, Wheelers Hill; Gordon F. Meijs, Elsternwick; San H. Thang, Oakleigh South, all of Australia

[73] Assignee: Commonwealth Scientific and Industrial Research Organisation, Campbell, Australia

[21] Appl. No.: 72,687

[22] Filed: Jun. 7, 1993

Related U.S. Application Data

[63] Continuation of Ser. No. 731,393, Jul. 17, 1991, abandoned, which is a continuation of Ser. No. 372,357, filed as PCT/AU87/412, Dec. 4, 1987, abandoned.

[30] Foreign Application Priority Data

Dec. 5, 1986 [AU] Australia ............... PH9351/86/AU
Aug. 19, 1987 [AU] Australia ............... PI3813/87

[51] Int. Cl.$^6$ ................................ C08F 2/38
[52] U.S. Cl. ........................ 526/240; 526/72; 526/278; 526/279; 526/286; 526/288; 526/289; 526/291; 526/292.1; 526/292.8; 526/292.9; 526/296; 526/304; 526/312; 526/313; 526/317.1; 526/320; 526/333
[58] Field of Search .............. 526/277, 278, 279, 240, 526/241, 289, 292.1, 296, 291, 72

[56] References Cited

U.S. PATENT DOCUMENTS

| | | | |
|---|---|---|---|
| 2,390,164 | 12/1945 | Moffett | 526/291 |
| 2,654,725 | 10/1953 | Price | 526/291 |
| 3,726,832 | 4/1973 | Komatsu | 526/173 |
| 3,736,302 | 5/1973 | Joh | 526/72 |
| 4,040,970 | 8/1977 | Tsuneda | 526/332 |
| 4,176,219 | 11/1979 | Makino | 526/92 |
| 4,405,742 | 9/1983 | Musch | 526/85 |
| 4,439,589 | 3/1984 | Alberts | 526/209 |
| 4,656,233 | 4/1987 | Hertler | 526/204 |

FOREIGN PATENT DOCUMENTS

| | | |
|---|---|---|
| 8386 | 5/1964 | Japan . |
| 664324 | 1/1952 | United Kingdom . |
| 666173 | 2/1952 | United Kingdom . |
| 1023901 | 3/1966 | United Kingdom . |

OTHER PUBLICATIONS

Chem Abst, 104, 110222x (1986).
Makromolekulare Chemie, 17(4), pp. 737-744 (1983).

*Primary Examiner*—Christopher Henderson
*Attorney, Agent, or Firm*—Bacon & Thomas

[57] ABSTRACT

A process for the production of polymers by free radical polymerization, characterized in that there is added to the polymerization system one or more compounds of the general formula (A).

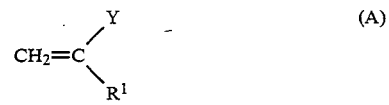

where R$^1$ is hydrogen or a group capable activating the vinylic carbon towards free radical addition;

Y is OR$^2$ or CH$_2$X(R$^2$)$_n$ where R$^2$ is an optionally substituted alkyl, optionally substituted alkenyl, optionally substituted alkynyl, or optionally substituted saturated, unsaturated or aromatic, aromatic carbocyclic or heterocyclic ring;

X is an element other than carbon selected from Groups IV, V, VI or VII of the Periodic Table or a group consisting of an element selected from Groups IV, V, or VI to which is attached one or more oxygen atoms; and n is a number from 0 to 3, such that the valency of the group X is satisfied and, when n is greater than 1, the groups represented by R$^2$ may be identical or different.

20 Claims, No Drawings

CONTROL OF MOLECULAR WEIGHT AND END-GROUP FUNCTIONALITY OF POLYMERS

This application is a continuation of application Ser. No. 07/731,393, filed Jul. 17, 1991, now abandoned which is a continuation of Ser. No. 07/372,357, filed as PCT/AU87/412, Dec. 4, 1987, now abandoned.

The invention relates to processes for radical-initiated polymerization of unsaturated species and for the control of molecular weight and end-group functionality of the polymeric products produced from such processes. Polymers of limited molecular weights, or oligomers, are useful as precursors in the manufacture of other polymeric materials and as additives in plastics, elastomerics, and surface-coating compositions, as well as being useful in their own right in many applications.

In conventional polymerization practice, the manufacture of oligomers requires the use of an initiator which acts as a free radical source, and of a chain transfer agent. The chain transfer agent controls the molecular weight of the polymer molecule by reacting with the propagating polymer radical to terminate its growth. It then initiates a new polymer chain thus transferring the growth process from one discrete polymer molecule to another discrete polymer molecule. At least a part of the chain transfer agent is incorporated into the polymer molecule and thus is consumed during the process. The incorporated residue of the chain transfer agent can lead to undesirable end-groups on the polymer.

The chain transfer agents most commonly used are alkanethiols, which possess an objectionable odour, lead to a wide distribution of molecular weight with certain monomers, do not allow the production of telechelic polymers, and offer limited scope for the preparation of polymers with a single functional end-group. Additionally, with thiols there is little scope for the chain transfer efficiency to be optimized for a particular polymerization.

The present invention provides a process for the production of lower molecular weight polymers by free radical polymerization, which process is characterized by the addition of compounds of the general Formula A to the polymerization system. The process can, by appropriate selection of the compound of Formula A, produce polymers with groups capable of further chemical reaction at one or both ends of the polymer chain.

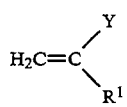

(A)

In Formula A, $R^1$ can be hydrogen, but preferably represents a group capable of activating the vinylic carbon towards free radical addition. Suitable groups are phenyl and optionally substituted aromatic groups, alkoxycarbonyl or aryloxycarbonyl (—COOR), carboxy (—COOH), acyloxy (—O$_2$CR), carbamoyl (—CONR$_2$) and cyano (—CN); AND Y is —CH$_2$X(R$^2$)$_n$ or —OR$^2$; WHERE $R^2$ represents optionally substituted alkyl, optionally substituted alkenyl, optionally substituted alkynyl, or optionally substituted saturated, unsaturated, or aromatic carbocyclic or heterocyclic ring; AND when Y is —CH$_2$X(R$^2$)$_n$, X represents an element other than carbon selected from groups IV, V, VI, or VII of the Periodic Table or a group consisting of an element selected from groups IV, V, or VI to which is attached one or more oxygen atoms. Suitable elements X include sulphur, silicon, selenium, phosphorus, bromine, chlorine, and tin. Examples of oxygen containing groups include phosphonates, sulphoxides, sulphones, and phosphine oxides; AND n is a number from 0 to 3, such that the valency of the group X is satisfied. When n is greater than 1, the groups represented by $R^2$ may be identical or different.

In Formula A, substituted rings may have a reactive substituent group directly or indirectly attached to the ring by means of a methylene group or other side-chain.

The reactive substituent groups referred to above for $R^1$ and/or $R^2$ in Formula A do not take part in the actual lowering of the molecular weight, but are installed at the ends of the polymer chains and may be capable of subsequent chemical reaction. The low molecular weight polymer containing said reactive group or groups is thereby able to undergo further chemical transformation, such as being joined with another polymer chain as described subsequently in this specification.

Suitable reactive substituents include: hydroxy (—OH); amino (—NH$_2$); halogen; phosphonate; trialkyoxysilyl; allyl; cyano (—CN); epoxy; and carboxylic acid (—COOH) and its derivatives, such as ester (—COOAlkyl). The substituents may alternatively be non-reactive such as alkoxy (—OAlkyl) or alkyl.

Alkyl groups referred to in this specification may contain from 1 to 32 carbon atoms. Alkenyl and alkynyl groups may contain from 2 to 32 carbon atoms. Saturated, unsaturated, or aromatic carbocyclic or heterocyclic rings may contain from 3 to 14 atoms.

The process of this invention uses the compounds of general Formula A as alternatives to thiols or other chain transfer agents for the control of molecular weight. The process of this invention may be operated in a similar manner to conventional processes using thiols. For example, the process described herein is applicable to the manufacture of synthetic rubbers and other polymer formulations, where reduced molecular weight aids processing and improves properties. The process can also be used to produce low molecular weight polymers and oligomers for a variety of applications, such as high-solids surface coatings, paints, and adhesives. For example, low molecular weight hydroxyacrylic polymers can be prepared using the compounds described in this invention and these can be later crosslinked by reaction with polyisocyanates.

Compounds of the general Formula A have the advantage of being simply prepared from inexpensive starting materials. Unlike thiols, they do not, in general, posses an objectionable odour. They exhibit an unexpectedly high activity in controlling molecular weight in polymerization reactions and are superior to thiols. Their activity is such that their chain transfer constants approach the optimum of 1.0 and this activity is not highly dependent, as it is with thiols, on the structure of the propagating radical. As is well known in the art, compounds with chain transfer constants close to this optimimum of 1.0 allow the production under convenient conditions of polymers of narrow molecular weight distribution. Additionally, when the chain transfer constant of a given compound with two or more monomers is reasonably close to 1, the distribution of molecular weights in copolymerizations of these monomers can more readily be controlled. The compounds of Formula A in general are superior to thiols inasmuch as their chain transfer constants are closer to 1.0. Additionally, with this invention there is scope for the chain transfer efficiency to be optimized for a particular polymerization by the appropriate choice of the substituent $R^1$ in Formula A. For example, when $R^1$ is electron deficient, the efficiency with electron donor monomers such as styrene is enhanced.

The process of this invention utilizing compounds of the general Formula I [Formula A, $Y=-CH_2X(R^2)_n$], unlike processes involving other chain transfer agents, directly produces polymers or oligomers containing a polymerizable olefinic group at one end and can be used to prepare macromonomers, which are useful materials for the preparation of graft copolymers by methods well known to the art.

When the process utilizes compounds of Formula I containing a reactive substituent group on at least one of the groups $R^2$, it may be used to produce polymers and oligomers with said reactive substituent on the end remote from the olefinic group. Polymers or oligomers with reactive substituents on one end may also be prepared when the process utilizes compounds of Formula I with reactive substituents on $R^1$ or when the process utilizes compounds of Formula II [Formula A, $Y=-OR^2$], containing reactive substituents on either $R^1$ or $R^2$. In this latter case using compounds of Formula II, the resultant low molecular weight polymers or oligomers contain no double bonds and, therefore, do not have the properties associated with a macromonomer. In a number of instances this is desirable, for example, in processes which are taken to very high conversion.

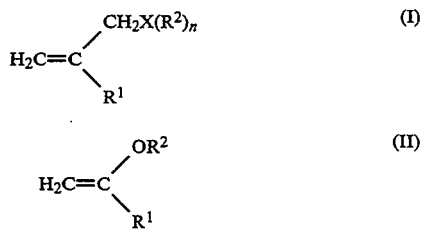

Mono-end-functional polymers or oligomers, produced by the process of this invention, may be linked by means of the introduced reactive substituent directly to a polymer backbone leading to graft copolymers. They may also be linked with other end-functional polymers or oligomers to form AB block copolymers or with suitable telechelic polymers or oligomers to form ABA block copolymers. Block copolymers are important as compatibilizing agents, adhesives, and in advanced surface coating formulations. Low molecular weight polymers and oligomers with one functional end-group may also possess desirable physical attributes in their own right, such as surface wetting properties.

The functional substituents installed at one or both ends of the polymer chains by the process described herein may be converted into other functional groups by performing chemical functional group transformations as is well known in the art. For example, ester functionality may be converted into carboxylic acid functionality by hydrolysis, tert-butyldimethylsilyloxy groups may be converted into hydroxy groups by treating the polymer with fluoride ion, and chloromethylphenyl groups may be treated with nucleophiles to afford a variety of other functional groups.

Mono-end-functional polymers or oligomers that do not contain a double bond may also be converted to macromonomers by methods well known to the art. For example, —OH or —COOH terminated polymers can be prepared using II in which $R^2$ carries hydroxyl or ester substituents. The hydroxy-terminated polymers may then be converted to macromonomers by reaction with acryloyl or methacryloyl chloride or similar reagents. In the case of —COOH terminated polymers, macromonomers can be prepared by reaction with glycidyl methacrylate or similar compounds. Such macromonomers by virtue of their chemical structure have differing reactivity in polymerization reactions compared with those produced directly by the process utilizing I.

When the compounds of Formula A contain reactive substituents on both $R^1$ and $R^2$, the process is particularly useful for the preparation of telechelic or di-end-functional polymers and oligomers. These products of the process are especially useful and have applications as crosslinking agents to produce polymer networks and as building blocks for the preparation of multicomponent polymer systems such as segmented and ABA block copolymers. For example, $\alpha,\omega$-dihydroxy oligomers or polymers can be reacted with the readily available $\alpha,\omega$-diisocyanato oligomers to produce segmented polyurethanes which are useful as elastomers and high impact strength materials for a range of applications.

The following compounds of Formula A are novel and form part of this invention:

α-(t-Butanethiomethyl)styrene
α-(n-Butanethiomethyl)styrene
α-(Carboxymethanethiomethyl)styrene
α-(Carboxyethanethiomethyl)styrene
α-(2-Hydroxyethanethiomethyl)styrene
α-(2-Aminoethanethiomethyl)styrene
α-[3-(Trimethoxysilyl)propanethiomethyl]styrene
α-(n-Butanesulphinylmethyl)styrene
Ethyl α-(t-Butanethiomethyl)acrylate
Ethyl α-(Carboxymethanethiomethyl)acrylate
α-(Carboxymethanethiomethyl)acrylic Acid
α-(Bromomethyl)acrylonitrile
α-(t-Butanethiomethyl)acrylonitrile
α-(Diethoxyphosphorylmethyl)styrene
α-(4-Methoxycarbonylbenzyloxy)styrene
α-Benzyloxy[4-(chloromethyl)styrene]
α-Benzyloxy[3-(chloromethyl)styrene]
α-(4-Cyanobenzyloxy)styrene
α-[4-(Hydroxymethyl)benzyloxy]styrene
α-[4-(Aminomethyl)benzyloxy]styrene
α-(4-Methoxybenzyloxy)styrene
α-Benzyloxy[4-(tert-butyldimethylsilyloxymethyl)styrene]
α-Benzyloxy[3-(tert-butyldimethylsilyloxymethyl)styrene]
α-Benzyloxy[4-(acetoxymethyl)styrene]
α-Benzyloxy[3-(acetoxymethyl)styrene]
α-Benzyloxy[4-(hydroxymethyl)styrene]
α-Benzyloxy[3-(hydroxymethyl)styrene]
α-Benzyloxy(4-chlorostyrene)
α-Benzyloxy(3-methoxystyrene)
α-Benzyloxy(4-methoxystyrene)
α-(4-Methoxycarbonylbenzyloxy)[4-(acetoxymethyl)styrene]
α-(4-Methoxycarbonylbenzyloxy)[3-(acetoxymethyl)styrene]

α-[4-(Hydroxymethyl)benzyloxy][4-(hydroxymethyl)styrene]

α-[4-(Hydroxymethyl)benzyloxy][3-(hydroxymethyl)styrene]

α-[4-(tert-Butyldimethylsilyloxymethyl)benzyloxy][4-(tert-butyldimethylsilyloxymethyl)styrene]

α-[4-(tert-Butyldimethylsilyloxymethyl)benzyloxy][3-(tert-butyldimethylsilyloxymethyl)styrene]

α-(4-Methoxycarbonylbenzyloxy)-4-cyanostyrene

α-[4-(Hydroxymethyl)benzyloxy][4-(aminomethyl)styrene]

α-Benzyloxyacrylonitrile

Methyl α-Benzyloxyacrylate

α-Benzyloxyacrylamide

The compounds of Formula II, described in the present invention, bear superficial resemblance to compounds of Formula III, which have been disclosed previously as chain transfer agents in the *Journal of Macromolecular Science—Chemistry*, 1984, A21, 979–995; "Ring Opening Polymerization: Kinetics, Mechanism, and Synthesis", ACS Symposium Series No. 286, J. E. McGrath, Ed., Washington D.C.: 1985, chapter 4; and in "Reactive Oligomers", ACS Symposium Series No. 282, F. W. Harris and H. J. Spinelli, Eds, Washington D.C., 1985, chapter 13.

(III)

In Formula III, $R^1$ and $R^2$ represent alkyl, benzyl, or substituted benzyl groups. The compounds of the present invention exhibit a much greater resistance to hydrolytic decomposition, than do those of Formula III. In fact, processes involving compounds of the Formula III, unlike those of the present invention, have little practical utility for control of molecular weight on account of this hydrolytic lability, except, perhaps, under conditions where the monomers and any solvents used, are most rigorously purified and maintained in a strictly anhydrous condition.

PREPARATION OF THE CHAIN TRANSFER AGENTS DESCRIBED IN THIS INVENTION

α-(Alkanethiomethyl)styrenes

These compounds (Formula I, X=sulphur, $R^1$=phenyl, $R^2$=substituted or unsubstituted alkyl, aryl, alkenyl, or alkynyl, n=1) can be readily prepared via a nucleophilic substitution reaction involving the treatment of a stirred alcoholic solution of α-(bromomethyl)styrene with the appropriate thiol and a base, such as potassium carbonate or hydroxide, or sodium acetate, hydroxide or methoxide. It is usually desirable to use an equimolar ratio of the reagents. The starting material α-(bromomethyl)styrene can be obtained using a procedure described in *The Journal of Organic Chemistry*, 1957, 22, 1113, or in the *Journal of the American Chemical Society*, 1954, 76, 2705.

α-(t-Butanethiomethyl)styrene (Formula I, X=sulphur, $R^1$=phenyl, $R^2$=t-butyl, n=1). [Typical procedure]. t-Butanethiol (4 ml, 35.5 mmol) was added slowly at room temperature to a stirred suspension of potassium carbonate (5 g, 36 mmol) and α-(bromomethyl)styrene (7 g, 35.5 mmol) in absolute ethanol [or methanol] (50 ml). Stirring was maintained for 16 h and then the reaction mixture was poured into water, and extracted (3×) with diethyl ether. The extracts were then dried over anhydrous $Na_2SO_4$, filtered, and evaporated to dryness. Distillation of the crude product through a short column afforded α-(t-butanethiomethyl)styrene (5 g, 69%) as a colourless liquid: bp 88° C./3 mmHg. $^1$H NMR ($CDCl^3$) δ 1.35 (9H, s, $(CH_3)_3C$), 3.60 (2H, s, allylic $CH_2S$), 5.30 (1H, s, olefinic proton), 5.40 (1H, s, olefinic proton), 7.20–7.50 (5H, m, aromatic protons); $^{13}C$ NMR ($CDCl_3$) δ 30.8, $(CH_3)_3C$; 33.4, allylic $CH_2S$; 42.7, $SC(CH_3)_3$; 115.0, $H_2\underline{C}{=}C$; 126.2, 127.7, 128.3, 144.8, aromatic ring carbons; 140.0, $H_2C{=}\underline{C}$; MS($CH_4$) 207 (MH+, 13%), 179 (26%), 151 (100%).

α-(n-Butanethiomethyl)styrene (Formula I, X=sulphur, $R^1$=phenyl, $R^2$=n-butyl, n=1). This compound was prepared using a similar procedure to that described above. Pure α-(n-butanethiomethyl)styrene was obtained in 90% yield after column chromatography on silica-gel (petroleum spirit eluent): $^1$H NMR ($CDCl_3$) δ 0.85 (3H, t, $CH_3CH_2$, J 7.0 Hz), 1.20–1.70 (4H, m, $CH_3CH_2CH_2CH_2S$), 2.45 (2H, t, $CH_2CH_2S$, J 7.0 Hz), 3.58 (2H, s, allylic $CH_2S$), 5.20 (1H, s, olefinic proton), 5.40 (1H, s, olefinic proton) 7.20–7.50 (5H, m, aromatic protons).

α-(Carboxymethanethiomethyl)styrene (Formula I, X=sulphur, $R^1$=phenyl, $R^2$=—$CH_2COOH$, n=1). A solution of α-(bromomethyl)styrene (7 g, 35.5 mmol) in methanol (15 ml) was added to a stirred solution at room temperature of sodium acetate (5.86 g, 71.4 mmol) and thioglycolic acid (6.57 g, 71.4 mmol) in methanol (25 ml). The mixture was allowed to stir for 2 days and then was poured into a mixture of water and saturated $NaHCO_3$ solution (1:1), and washed with diethyl ether. The aqueous basic layer was adjusted to pH 1 with hydrochloric acid and then extracted three times with diethyl ether. The combined ether layers were then dried over anhydrous $MgSO_4$. After removal of the solvent, the required compound (7.1 g, 95.5%) was obtained, mp 74°–76° C. (from $CCl_4$); $^1$H NMR ($CDCl_3$) δ 3.20 (2H, s, $SCH_2COOH$), 3.70 (2H, s, allylic $CH_2S$), 5.25 (1H, s, olefinic proton), 5.50 (1H, s, olefinic proton), 7.20–7.50 (5H, m, aromatic protons), 10.80 (1H, broad singlet, COOH); MS ($CH_4$) 209 (MH+, 100%), 191 (50%), 163 (91%), 117 (96%).

α-(Carboxyethanethiomethyl)styrene (Formula I, X=sulphur, $R^1$=phenyl, $R^2$=—$CH_2CH_2COOH$, n=1). Similarly, treatment of α-(bromomethyl)styrene with 3-mercaptopropionic acid and sodium acetate in methanol as described above, afforded α-(carboxyethanethiomethyl)styrene: mp 47°–49° C. (from $CCl_4$); $^1$H NMR ($CDCl_3$) δ 2.60–2.90 (4H, m, $SCH_2CH_2COOH$), 3.60 (2H, s, allylic $CH_2S$), 5.25 (1H, s, olefinic proton), 5.45 (1H, s, olefinic proton), 7.20–7.50 (5H, m, aromatic protons), 8.35 (1H, broad singlet, COOH).

α-(2-Hydroxyethanethiomethyl)styrene (Formula I, X=sulphur, $R^1$=phenyl, $R^2$=—$CH_2CH_2OH$, n=1). The title compound was prepared in 90% yield after column chromatography on silica gel (ethyl acetate/petroleum spirit). $^1$H NMR ($CDCl_3$) δ 2.35 (1H, broad singlet, OH), 2.65 (2H, t, $SCH_2CH_2OH$, J 7.0 Hz), 3.60 (2H, s, allylic $CH_2S$), 3.68 (2H, t, $SCH_2CH_2OH$, J 7.0 Hz), 5.30 (1H, s, olefinic proton), 5.45 (1H, s, olefinic proton), 7.20–7.50 (5H, m, aromatic protons); $^{13}C$ NMR ($CDCl_3$) δ 34.4, allylic $CH_2S$; 36.1, $\underline{S}CH_2CH_2OH$; 60.2, $SCH_2\underline{C}H_2OH$; 115.3, $H_2\underline{C}{=}C$; 126.3, 128.0, 128.4, 143.6, aromatic ring carbons; 139.0, $H_2C{=}\underline{C}$; MS ($CH_4$) 195 MH+, 40%), 177 (100%), 149 (69%), 135 (42%), and 119 (87%).

α-(2-Aminoethanethiomethyl)styrene (Formula I, X=sulphur, R$^1$=phenyl, R$^2$=—CH$_2$CH$_2$NH$_2$, n=1). A solution of α-(bromomethyl)styrene (0.5 g, 2.55 mmol) in methanol (2 ml) was added to a cold stirred solution of 2-aminoethanethiol (0.197 g, 2.55 mmol) and sodium methoxide (0.165 g, 3 mmol) in methanol (3 ml). After 15 minutes at 0° C., the mixture was allowed to stir at room temperature for a further one hour. The resulting mixture was then poured into water and acidified with dilute HCl, and then extracted with diethyl ether in order to remove traces of the unreacted bromide. The acidic layer was then brought to pH 7–8 with KOH solution (5%) and then extracted immediately with diethyl ether (3×). The combined ether extracts were then dried (Na$_2$SO$_4$). After removal of the solvent, the product, α-(2-aminoethanethiomethyl)styrene, (0.42 g, 85%) was obtained as a brownish liquid: $^1$H NMR (CDCl$_3$) δ 1.75 (2H, broad singlet, NH$_2$), 2.45–2.85 (4H, A$_2$B$_2$ multiplets, SCH$_2$CH$_2$NH$_2$), 3.55 (2H, m, allylic CH$_2$S), 5.15 (1H, m, olefinic proton), 5.40 (1H, m, olefinic proton), 7.20–7.50 (5H, m, aromatic protons); MS (CH$_4$) 194 (MH$^+$, 6%), 177 (100%), 149 (54%).

α-[3-(Trimethoxysilyl)propanethiomethyl]styrene (Formula I, X=sulphur, R$^1$=phenyl, R$^2$=—CH$_2$CH$_2$CH$_2$Si(OCH$_3$)$_3$, n=1). This compound was prepared in 94% yield after rapid column chromatography on silica gel (ethyl acetate). $^1$H NMR (CDCl$_3$) δ 0.75 (2H, t, CH$_2$Si, J 7.0 Hz), 1.75 (2H, quintet, SCH$_2$CH$_2$CH$_2$Si), 2.55 (2H, t, SCH$_2$CH$_2$CH$_2$Si, J 7.0 Hz), 3.60 (2H, s, allylic CH$_2$S), 3.60 (9H, s, 3×OCH$_3$), 5.20 (1H, s, olefinic proton), 5.45 (1H, s, olefinic proton), 7.20–7.50 (5H, m, aromatic protons).

α-(n-Butanesulphinylmethyl)styrene (Formula I, X=S(O), R$^1$=phenyl, R$^2$=n-butyl, n=1). To a stirred solution of α-(n-butanethiomethyl)styrene (1 g, 4.85 mmol) in CH$_2$Cl$_2$ (25 ml) at −78° C., a solution of m-chloroperbenzoic acid 90% (0.93 g, 5.40 mmol) in CH$_2$Cl$_2$ (25 ml) was added dropwise. The mixture was allowed to stir at −78° C. for 1 h before being poured into aqueous saturated NaHCO$_3$ (50 ml). The organic layer was separated and the aqueous phase was extracted three times with CH$_2$Cl$_2$. The combined organic phases were then washed with water, dried over anhydrous Na$_2$SO$_4$, filtered, and the solvent was removed to give α-(n-butanesulphinylmethyl)styrene (1.05 g, 97%): mp 42°–43.5° C. (from petroleum spirit); $^1$H NMR (CDCl$_3$) δ 0.90 (3H, t, CH$_2$CH$_3$, J 7.0 Hz), 1.20–1.90 (4H, m, CH$_2$CH$_2$CH$_2$CH$_3$), 2.65 (2H, t, S(O)CH$_2$CH$_2$, J 7.0 Hz), 3.90 (2H, AB quartet, allylic CH$_2$S(O), J$_{AB}$ 15.0 Hz), 5.35 (1H, s, olefinic proton), 5.55 (1H, s, olefinic proton), 7.20–7.50 (5H, m, aromatic protons); IR (film) 1040 cm$^{-1}$ (S—O); MS (CH$_4$) 223 (MH$^+$, 100%), 117 (15%).

Alkyl α-(Alkanethiomethyl)acrylates

In principle, these compounds (Formula I, X=sulphur, R$^1$=—COOAlkyl, R$^2$=substituted or unsubstituted alkyl, aryl, alkenyl, or alkynyl, n=1) could be prepared directly via reaction of an alkyl α-(bromomethyl)-acrylate, the appropriate thiol, and a base. However, an alternative and generally more useful preparation, which is outlined in *The Journal of the Chemical Society, Perkin Transactions I*, 1986, 1613–1619, can be conveniently used to prepare the following compounds.

Ethyl α-(t-Butanethiomethyl)acrylate (Formula I, X=sulphur, R$^1$=—COOCH$_2$CH$_3$, R$^2$=t-butyl, n=1) has been previously reported in the article cited above.

Ethyl α-(Carboxymethanethiomethyl)acrylate (Formula I, X=sulphur, R$^1$=—COOCH$_2$CH$_3$, R$^2$=—CH$_2$COOH, n=1). Thioglycolic acid (2.0 g, 22 mmol) was added slowly to a stirred suspension of ethyl 1,3-dibromopropane-2-carboxylate (6.0 g, 21.9 mmol) and potassium carbonate (3.04 g, 22 mmol) in absolute ethanol (25 ml). After 2 h of stirring at ambient temperature, the mixture was poured into saturated aqueous NaHCO$_3$, and washed with diethyl ether. The aqueous layer was acidified with dilute HCl and then extracted (5×) with diethyl ether. The combined ether extracts were then dried over anhydrous Na$_2$SO$_4$. After the solvent was removed, vacuum distillation of the crude product afforded pure ethyl α-(carboxymethanethiomethyl)acrylate (1.3 g, 29%), as a slightly yellow liquid, bp 122°–130° C. (0.05 mmHg), which solidified upon cooling in the freezer. $^1$H NMR (CDCl$_3$) δ 1.30 (3H, t, OCH$_2$CH$_3$, J 7.0 Hz), 3.20 (2H, s, SCH$_2$COOH), 3.55 (2H, s, allylic CH$_2$S), 4.25 (2H, q, OCH$_2$CH$_3$, J 7.0 Hz), 5.65 (1H, s, olefinic proton), 6.25 (1H, s, olefinic proton), 10.55 (1H, broad s, exchangeable, COOH).

α-(Alkanethiomethyl)acrylic Acids

These compounds (Formula I, X=sulphur, R$^1$=—COOH, R$^2$=substituted or unsubstituted alkyl, aryl, alkenyl, or alkynyl, n=1) can be prepared directly from the corresponding esters [alkyl α-(alkanethiomethyl)acrylates, prepared as described above] by treatment with aqueous KOH.

α-(Carboxymethanethiomethyl)acrylic Acid (Formula I, X=sulphur, R$^1$=—COOH, R$^2$=—CH$_2$COOH, n=1). This compound was prepared from ethyl α-(carboxymethanethiomethyl)acrylate (0.5 g, 2.45 mmol) and aqueous KOH (4% solution, 20 ml). The mixture was allowed to stir at room temperature overnight and then brought to pH 1 with hydrochloric acid. The resultant mixture was extracted with diethyl ether (5×). The combined extracts were then dried over anhydrous Na$_2$SO$_4$. After the solvent was removed, the product, α-(carboxymethanethiomethyl)acrylic acid (0.42 g, 97%), solidified. mp 121°–125° C.; $^1$H NMR (CD$_3$OD) δ 3.20 (2H, s, SCH$_2$COOH), 3.50 (2H, s, allylic CH$_2$S), 4.90 (2H, broad singlet, 2×COOH), 5.70 (1H, s, olefinic proton), 6.20 (1H, s, olefinic proton). IR (KBr) 2500–3500 (broad), 1680, 1700 cm$^{-1}$ (C=O). MS (CH$_4$) 177 (MH$^+$, 5%), 159 (47%), 131 (1001%).

α-(Alkanethiomethyl)acrylonitriles

In general, these compounds (Formula I, X=sulphur, R$^1$=—CN, R$^2$=substituted or unsubstituted alkyl, aryl, alkenyl, or alkynyl, n=1) can be prepared by reaction of a cooled, stirred alcoholic solution of α-(bromomethyl)acrylonitrile with the appropriate thiol and a base.

The starting material, α-(bromomethyl)acrylonitrile, was obtained using a similar procedure to that described for the syntheses of ethyl α-(hydroxymethyl)acrylate and ethyl α-(halomethyl)acrylates in *Synthesis*, 1982, 924–926. Thus, α-(hydroxymethyl)acrylonitrile (bp 68°–70° C. (0.3 mmHg)) was stirred with phosphorus tribromide in dry ether at −10° C. to afford α-(bromomethyl)acrylonitrile, bp 45°–47° C. (2 mmHg); $^1$H NMR (CDCl$_3$) δ 3.85 (2H, broad singlet, allylic CH$_2$Br), 5.95 (2H, m, olefinic protons).

α-(t-Butanethiomethyl)acrylonitrile (Formula I, X=sulphur, R$^1$=—CN, R$^2$=t-butyl, n=1). α-(Bromomethyl)acrylonitrile (1.18 g, 8 mmol) was converted to the title compound by treatment with a mixture of t-butanethiol (0.9 ml, 8 mmol), potassium carbonate (1.12 g, 8.1 mmol) and absolute ethanol (10 ml) at 0° C. for 1 h. The resulting mixture was allowed to stand at room temperature for another hour before the usual workup. After column chromatography on silica-gel (8% ethyl acetate/petroleum spirit), α-(t-butanethiomethyl)acrylonitrile (0.97 g, 77%) was obtained as a colourless liquid: $^1$H NMR (CDCl$_3$) δ 1.35 (9H, s, (CH$_3$)$_3$C), 3.35 (2H, m, allylic CH$_2$S), 5.95 (2H, m, olefinic protons); MS (CH$_4$) 156 (MH$^+$, 34%), 128 (55%), 100 (100%).

α-(Diethoxyphosphorylmethyl)styrene (Formula I, X=P(O), R$^1$=phenyl, R$^2$=—OCH$_2$CH$_3$, n=2). α-(Bromomethyl)styrene was treated with an equimolar ratio of triethylphosphite at reflux for 1 h. After the mixture was cooled to room temperature, the by-product, ethyl bromide, was removed under reduced pressure, and the product α-(diethoxyphosphorylmethyl)styrene was obtained in quantitative yield as a yellowish syrup: $^1$H NMR (CDCl$_3$) δ 1.20 (6H, t, 2×OCH$_2$CH$_3$, J 7.5 Hz), 3.05 (2H, d, CH$_2$P(O), J 22.5 Hz), 4.00 (4H, m, 2×OCH$_2$CH$_3$), 5.35 (1H, d, olefinic proton, J 6.0 Hz), 5.50 (1H, d, olefinic proton, J 6 Hz), 7.25–7.55 (5H, m, aromatic protons).

The following three chain transfer agents used in this invention were prepared according to literature procedures.

Ethyl α-(Trimethylsilymethyl)acrylate (Formula I, X=Si, R$^1$=—COOCH$_2$CH$_3$, R$^2$=—CH$_3$, n=3) as described in *Synthesis*, 1985, 271–272.

Ethyl α-(Benzenesulphonylmethyl)acrylate (Formula I, X=S(O)$_2$, R$^1$=—COOCH$_2$CH$_3$, R$^2$=phenyl, n=1) as described in *Journal of the Chemical Society, Chemical Communications*, 1986, 1339–1340. This compound was purified either by high vacuum distillation (bp 136°–140° C./0.05 mmHg) or by chromatography on silica-gel (ethyl acetate:petroleum 2:3). $^1$H NMR (CDCl$_3$) δ 1.20 (3H, t, OCH$_2$CH$_3$, J 7.5 Hz), 4.05 (2H, q, OCH$_2$CH$_3$, J 7.5 Hz), 4.20 (2H, s, allylic CH$_2$S(O)$_2$), 5.90 (1H, s, olefinic proton) 6.50 (1H, s, olefinic proton), 7.40–8.00 (5H, m, aromatic protons).

Ethyl α-(Tri-n-butylstannylmethyl)acrylate (Formula I, X=Sn, R$^1$=—COOCH$_2$CH$_3$, R$^2$=n-butyl, n=3). This compound was prepared from ethyl α-(benzenesulphonylmethyl)acrylate, n-Bu$_3$SnH and AIBN in benzene at 80° C. for 1.5 h according to the procedure described in *Journal of the Chemical Society, Chemical Communications*, 1986, 1339–1340. $^1$H NMR (CDCl$_3$) δ 0.85–1.65 (30H, m, 3×CH$_2$CH$_2$CH$_2$CH$_3$, OCH$_2$CH$_3$), 2.00 (2H, s, allylic CH$_2$Sn), 4.15 (2H, q, OCH$_2$CH$_3$, J 7.5 Hz), 5.25 (1H, s, olefinic proton), 5.75 (1H, s, olefinic proton).

α-Alkoxystyrenes (Formula II, R$^1$=phenyl).

One class of compound used in this invention, the α-alkoxystyrenes (Formula II; R$^1$=phenyl) can be cheaply and easily prepared from styrene, the appropriate alcohol, iodine and mercuric oxide, using a procedure based on that described in *Die Makromolekulare Chemie*, 1967, 103, 68. This procedure is useful as a general synthesis and a number of derivatives can be prepared, including those with substituents on the phenyl group of the styrene or on R$^2$. It is usually desirable to use an equimolar ratio of the reagents and to add a non-reactive solvent such as petroleum ether or diethyl ether. When the compound II contains certain functional groups, the procedure is best modified to use an alkoxide base, such as sodium methoxide (Method A) or potassium tertbutoxide (Method B), or an amine base (Method C) in the elimination step. The compounds can be purified by chromatography on basic alumina or, in some cases, by recrystallization or by distillation at reduced pressures. An alternative, but more costly method of synthesis is to react the appropriate ester with a titanium-aluminium complex, as described in *The Journal of Organic Chemistry*, 1985, 50, 1212.

General Procedure for the Preparation of an α-Alkoxystyrene by Method A: α-(4-Methoxycarbonylbenzyloxy)styrene (Formula II, R$^1$=phenyl, R$^2$=CH$_3$OC(O)C$_6$H$_4$CH$_2$—). Iodine (6.35 g, 25 mmol) was added in small portions to a stirred suspension, maintained between 0° and 10° C., of yellow mercuric oxide (5.34 g, 25 mmol), styrene (2.6 g, 25 mmol), and methyl 4-(hydroxymethyl)benzoate (4.15 g, 25 mmol) in ether (5 ml). The resulting mixture was stirred for 1 h at 0° C. and then warmed to ambient temperature and stirred for a further 1 h. The mixture was then diluted with ether, and filtered. The filtrate was washed successively with water, aqueous sodium thiosulphate solution and a further two portions of water, and then dried (MgSO$_4$). The solvent was removed to afford the intermediate iodoether which was converted to the alkoxystyrene by addition to a boiling solution of sodium methoxide in methanol [prepared from sodium (1.15 g, 50 mmol) and methanol (25 ml)]. After the resulting mixture had been heated for 1 h under reflux, it was cooled, diluted with water and extracted with ether. The organic layer was washed with water and dried (K$_2$CO$_3$). After removal of the solvent, the crude mixture was chromatographed on basic alumina (30% CH$_2$Cl$_2$/petroleum spirit) to afford α-(4-methoxycarbonylbenzyloxy)styrene (1.3 g, 20%): $^1$H NMR (CDCl$_3$) δ 3.85 (3H, s), 4.24 (1H, d, J 3 Hz), 4.72 (1H, d, J 3 Hz), 4.97 (2H, s), 7.2–7.7 (7H, m), 8.03 (2H, d, J 8 Hz); MS (CH$_4$) 269 (MH$^+$, 15%), 149 (100%); IR (film) 1735 cm$^{-1}$.

General Procedure for the Preparation of an α-Alkoxystyrene by Method B: α-Benzyloxy[4-(chloromethyl)styrene] and α-Benzyloxy[3-(chloromethyl)styrene] (Formula II, R$^1$=ClCH$_2$C$_6$H$_4$—, R$^2$=benzyl). Treatment of a 2:3 mixture (7.63 g, 50 mmol) of 4-(chloromethyl)styrene and 3-(chloromethyl)styrene with benzyl alcohol (5.4 g, 50 mmol), iodine (12.7 g, 50 mmol), and mercuric oxide (10.8 g, 50 mmol), as described above, afforded the intermediate iodoether (18 g). Potassium tertbutoxide (0.28 g, 2.5 mmol) was added to a solution of the iodoether (0.48 g, 1.2 mmol) in ether (10 ml) and the mixture was allowed to stir at room temperature for 2 h. The mixture was then poured into saturated sodium chloride solution and water (1:1) and extracted three times with 50% ether/petroleum spirit. The combined extracts were washed with water and dried (K$_2$CO$_3$) to afford, after chromatography as described above, the required alkoxystyrene (260 mg): $^1$H NMR δ 4.33 (1H, d, J 1.9 Hz), 4.53 (2H, s), 4.73 (1H, d, J 1.9 Hz), 4.93 (2H, s), 7.1–7.7 (9H, m); MS (CH$_4$) 259, 261 (3:1, MH$^+$, 1%), 91 (100%).

General Procedure for the Preparation of an α-Alkoxystyrene by Method C: α-(4-Cyanobenzyloxy)styrene. (Formula II, R$^1$=phenyl, R$^2$=4-NCC$_6$H$_4$CH$_2$—). Treatment of 4-cyanobenzyl alcohol (5.98 g, 45 mmol) [prepared by sodium borohydride reduction (2 h, 20° C., EtOH) of 4-cyanobenzaldehyde] with styrene, iodine, and mercuric oxide, as described above, afforded the intermediate iodoether (9 g, 55%). 1,5-Diazabicyclo[4.3.0]non-5-ene (DBN) (3.5 g, 28 mmol) was added to a stirred suspension of the iodoether (8.5 g, 23 mmol), powdered potassium carbonate (2.12 g, 35 mmol), and acetonitrile (12 ml). After the resultant mixture was stirred at ambient temperature overnight, it was diluted with water and extracted twice with ether. The combined ether extracts were washed with water and aqueous sodium bicarbonate solution, dried ($K_2CO_3$), and purified by chromatography on alumina to afford the required compound (3.5 g, 65%), which was further purified by recrystallization ($CH_2Cl_2$/petroleum spirit): mp 54°-55° C.; $^1H$ NMR δ 4.20 (1H, d, J 3 Hz), 4.67 (1H, d, J 3 Hz), 4.95 (2H, s), 7.1-7.7 (9H, m).

The following compounds were also prepared.

α-[4-(Hydroxymethyl)benzyloxy]styrene (Formula II, $R^1$=phenyl, $R^2$=4-$HOCH_2C_6H_4CH_2$—). This compound was prepared by lithium aluminium hydride reduction of α-(4-methoxycarbonylbenzyloxy)styrene: $^1H$ NMR ($CCl_4$) δ 2.65 (1H, t, J 4.5 Hz), 4.15 (1H, d, J 3 Hz), 4.43 (2H, d, J 4.5 Hz), 4.60 (1H, d, J 3 Hz), 4.80 (2H, s), 7.1-7.7 (9H, m).

α-[4-(Aminomethyl)benzyloxy]styrene (Formula II, $R^1$=phenyl, $R^2$ =4-$H_2NCH_2C_6H_4CH_2$—). Lithium aluminium hydride reduction of α-(4-cyanobenzyloxy)styrene led to this compound: $^1H$ NMR ($CD_3OD$) δ 3.73 (2H, br s), 4.30 (1H, d, J 3 Hz), 4.70 (1H, d, J 3 Hz), 4.72 (2H, s), 4.87 (2H, s), 7.1-7.7 (9H, m).

α-(4-Methoxybenzyloxy)styrene (Formula II, $R^1$=phenyl, $R^2$=4-$CH_3OC_6H_4CH_2$—). Prepared using Method A. $^1H$ NMR ($CDCl_3$) δ 3.73 (3H, s), 4.28 (1H, d, J 3 Hz), 4.70 (1H, d, J 3 Hz), 4.83 (2H, s), 6.7-7.7 (9H, m); MS ($CH_4$) 241 ($MH^+$, 8%), 121 (100%).

α-Benzyloxy[4-(tert-butyldimethylsilyloxymethyl)styrene] and α-Benzyloxy[3-(tert-butyldimethylsilyloxymethyl)styrene)] (Formula II, $R^1$=(tert-butyldimethylsilyloxymethyl)phenyl, $R^2$=benzyl). (Hydroxymethyl)styrene was prepared from (chloromethyl)styrene (a 2:3 mixture of para and meta isomers) by a sequence described in *Polymer*, 1973, 14, 330. It was treated with tert-butyldimethylsilyl chloride following the general directions found in *Journal of the American Chemical Society*, 1972, 94, 6190. Method C was used to convert the resulting compound to the required alkoxystyrene: $^1H$ NMR ($CCl_4$) δ 0.70 (6H, s), 0.94 (9H, s), 4.17 (1H, d, J 2.4 Hz), 4.63 (3H, broadened s), 4.83 (2H, s), 7.0-7.6 (9H, m); MS ($CH_4$) 355 ($MH^+$, 4%), 91 (100%).

α-Benzyloxy[4-(acetoxymethyl)styrene] and α-Benzyloxy[3-(acetoxymethyl)styrene] (Formula II, $R^1$=$CH_3COOCH_2C_6H_4$-, $R^2$=benzyl). (Acetoxymethyl)styrene was prepared from (chloromethyl)styrene by the method described in *Polymer*, 1973, 14, 330. It was converted (Method C) to the required alkoxystyrene: $^1H$ NMR ($CCl_4$) δ 2.02 (3H, s), 4.23 (1H, d, J 2 Hz), 4.67 (1H, d, J 2 Hz), 4.87 (2H, s), 5.00 (2H, s), 7.0-7.7 (9H, m); MS ($CH_4$) 283 ($MH^+$, 1%), 91 (100%); IR 1740 $cm^{-1}$.

α-Benzyloxy[4-(hydroxymethyl)styrene] and α-Benzyloxy[3-(hydroxymethyl)styrene] (Formula II, $R^1$=$HOCH_2C_6H_4$—, $R^2$=benzyl). These compounds were obtained by lithium aluminium hydride reduction of α-benzyloxy[(acetoxymethyl)styrene]. $^1H$ NMR ($CCl_4$) δ 2.96 (1H, t, J 4.5 Hz), 4.20 (1H, d, J 2.5 Hz), 4.40 (2H, d, J 4.5 Hz), 4.63 (1H, d, J 2.5 Hz), 4.85 (2H, s), 7.0-7.8 (9H, m); IR 3320 (broad) $cm^{-1}$.

α-Benzyloxy(4-chlorostyrene) (Formula II, $R^1$=4-$ClC_6H_4$—, $R^2$=benzyl). Prepared using Method A. $^1H$ NMR ($CDCl_3$) δ 4.20 (1H, d, J 3 Hz), 4.63 (1H, d, J 3 Hz), 4.80 (2H, s), 7.0-7.6 (9H, m); MS ($CH_4$) 245, 247 (3:1, $MH^+$, 1%), 91 (100%).

α-Benzyloxy(3-methoxystyrene) (Formula II, $R^1$=3$CH_3OC_6H_4$—, $R^2$=benzyl). Prepared using Method A. $^1H$ NMR ($CDCl_3$) δ 3.74 (3H, s), 4.30 (1H, d, J 3 Hz), 4.71 (1H, d, J 3 Hz), 4.92 (2H, s), 6.7-6.9 (1H, m), 7.1-7.5 (8H, m); MS ($CH_4$) 241 ($MH^+$, 11%), 91 (100%).

α-Benzyloxy(4-methoxystyrene). (Formula II, $R^1$=4$CH_3OC_6H_4$—, $R^2$=benzyl). Prepared using Method A. $^1H$ NMR ($CDCl_3$) δ 3.70 (3H, s), 4.30 (1H, d, J 3 Hz), 4.60 (1H, d, J 3Hz), 4.90 (2H, s), 6.6-7.6 (9H, m).

α-(4-Methoxycarbonylbenzyloxy)[4-(acetoxymethyl)styrene] and
α-(4-Methoxycarbonylbenzyloxy)[3-(acetoxymethyl)styrene]. (Formula II, $R^1$=$CH_3COOCH_2C_6H_4$-, $R^2$=4-$CH_3OC(O)C_6H_4CH_2$—). Prepared using Method C. $^1H$ NMR ($CCl_4$) δ 1.98 (3H, s), 3.80 (3H, s), 4.20 (1H, d, J 3 Hz), 4.68 (1H, d, J 3 Hz), 4.8-5.0 (4H, m), 7.1-8.0 (8H, m).

α-[4-(Hydroxymethyl)benzyloxy][4-(hydroxymethyl)styrene] and
α-[4-(Hydroxymethyl)benzyloxy][3-(hydroxymethyl)styrene] (Formula II, $R^1$=$HOCH_2C_6H_4$—, $R^2$=$HOCH_2C_6H_4CH_2$—). Lithium aluminium hydride reduction of α-(4-methoxycarbonylbenzyloxy)[4-(acetoxymethyl)styrene] and α-(4-methoxycarbonylbenzyloxy)[3-(acetoxymethyl)styrene] gave the required compounds: $^1H$ NMR ($CD_3OD$) δ 4.33 (1H, d, J 2 Hz), 4.58 (4H, s), 4.77 (3H, broadened s), 4.92 (2H, s), 7.1-7.7 (8H, m).

α-[4-(tert-Butyldimethylsilyloxymethyl)-benzyloxy][4-(tert-butyldimethylsilyloxymethyl)styrene] and α-[(tert-Butyldimethylsilyloxymethyl)-benzyloxy][3-(tert-butyldimethylsilyloxymethyl)styrene]. (Formula II, $R^1$=tert-butyldimethylsilyloxymethylphenyl, $R^2$=4-tert-butyldimethylsilyloxymethylbenzyl).
Methyl 4-(hydroxymethyl)benzoate was treated with tert-butyldimethylsilyl chloride using the general procedure described in *Journal of the American Chemical Society*, 1972, 94, 6190. The resulting product was reduced with lithium aluminium hydride to afford 4-(tert-butyldimethylsilyloxymethyl)benzyl alcohol. This alcohol was converted into the required compound using Method C. $^1H$ NMR ($CCl_4$) δ 0.08 (12H, s), 0.91 (18H, s), 4.22 (1H, d, J 2 Hz), 4.68 (5H, br s), 4.90 (2H, s), 7.1-7.6 (8H, m); MS ($CH_4$) 483 ($M^+$-$CH_3$, 52%), 133 100%).

α-(4-Methoxycarbonylbenzyloxy)-4-cyanostyrene (Formula II, $R^1$=4-$NCC_6H_4$—, $R^2$4-$CH_3OC(O)C_6H_4CH_2$—). Prepared using Method C. $^1H$ NMR ($CCl_4$) δ 3.85 (3H, s), 4.23 (1H, d, J 3 Hz), 4.65 (1H, d, J 3 Hz), 4.97 (2H, s), 7.0-8.1 (8H, m).

α-[4-(Hydroxymethyl)benzyloxy]]4-(aminomethyl)styrene] (Formula II, $R^1$=4-$H_2NCH_2C_6H_4$—, $R^2$=4-$HOCH_2C_6H_4CH_2$—). Lithium aluminium hydride reduction of α-(4-methoxycarbonylbenzyloxy)-4-cyanostyrene gave the required compound. $^1H$ NMR ($CD_3OD$) δ 4.35 (1H, d, J 3 Hz), 4.58 (2H, s), 4.77 (6H, broadened s), 4.93 (2H, s), 7.0-7.7 (8H, m).

α-Alkoxyacrylonitriles

These compounds (Formula II, $R^1$=—CN) were prepared by a short sequence described in *The Journal of the Chemical Society*, 1942, 520, using the appropriate alcohol. The elimination step was best accomplished by stirring of the intermediate halocompound at ambient temperatures in acetonitrile containing 2 molar equivalents of DBN (1,5-diazabicyclo[4.3.0]non-5-ene) and 1.1 molar equivalents of potassium carbonate (similar to Method B, above).

α-Benzyloxyacrylonitrile (Formula II, $R^1$=—CN, $R^2$=benzyl). This compound, which had not previously been reported, was obtained using the above procedure. bp 55°–58° C. (0.025 mmHg); $^1$H NMR (CDCl$_3$) δ 4.83 (2H, s), 4.93 and 5.00 (2H, ABq, $J_{AB}$ 3 Hz), 7.33 (5H, s); MS (CH$_4$) m/e 160 (MH$^+$, 71%), 91 (100%); IR 2235 cm$^{-1}$.

α-Alkoxyacrylates.

These compounds (Formula II; $R^1$=—COOAlkyl) can be prepared from esters of 2,3-dibromopropionic acid by treatment with alkoxides, following the procedure described in *Bulletin of the Chemical Society of Japan*, 1970, 43, 2987. An alternative and generally more useful preparation is from a precursor to the corresponding nitrile (Formula II; $R^1$=—CN) by treatment with gaseous hydrogen chloride and a solution containing the appropriate alcohol, based on the procedure outlined in *Bulletin of the Chemical Society of Japan*, 1969, 42, 3207.

Methyl α-Benzyloxyacrylate (Formula II, $R^1$=CH$_3$OC(O)—, $R^2$=benzyl). A slow stream of hydrogen chloride gas was passed for 4 h through a solution of 2-benzyloxy-3-bromopropionitrile (16.75 g) in methanol (2.38 g) and ether (66 ml) which was maintained at −10° C. The mixture was allowed to stand at 5° C. overnight, and then ice was added in small portions to the mixture at 0° C. After 20 min of stirring, the mixture was poured into water and the product was extracted with ether, washed with water and aqueous sodium bicarbonate, and dried (MgSO$_4$). After the solvent was removed, the crude product was recrystallized from ether/CH$_2$Cl$_2$ to afford, after a first crop of crystals of 2-benzyloxy-3-bromopropanamide, the required intermediate, methyl 2-benzyloxy-3-bromopropanoate. This bromoester was treated with DBN/potassium carbonate as described above to yield methyl α-benzyloxyacrylate, mp 44.5°–45.5° C. (from hexane); $^1$H NMR δ 3.80 (3H, s), 4.63 (1H, d, J 3 Hz), 4.83 (2H, s), 5.37 (1H, d, J 3 Hz), 7.33 (5H, s); IR 1740 cm$^{-1}$. Ketals of alkyl pyruvates, prepared according to the directions in *The Journal of Organic Chemistry*, 1967, 32,1615, also may be converted to α-alkoxyacrylates by an acidic catalyst, as described in *Chemische Berichte*, 1911, 44, 3514.

α-Alkoxyacrylamides.

α-Benzyloxyacrylamide (Formula II, $R^1$=—CONH$_2$, $R^2$=benzyl). Treatment of 2-benzyloxy-3-bromopropanamide with DBN/potassium carbonate following the general procedure of Method C (above) yielded α-benzyloxyacrylamide (Formula II; $R^1$=—CONH$_2$), mp 132°–133° C.; $^1$H NMR (CDCl$_3$) δ 4.53 (1H, d, J 3 Hz), 4.80 (2H, s), 5.43 (1H, d, J 3 Hz), 6.50 (2H, br s), 7.33 (5H, s).

The following examples illustrate the use of the invention to produce polymers of controlled molecular weight and end-group functionality.

EXAMPLES OF THE PROCESS

Example 1

Preparation of Low Molecular Weight Olefin-Terminated Polymers of Methyl Methacrylate Using α-(t-Butanethiomethyl)styrene (Formula I, X=sulphur, $R^1$=phenyl, $R^2$=t-butyl, n=1).

Azobisisobutyronitrile (AIBN) (49.5 mg) was dissolved in freshly distilled methyl methacrylate (25 ml). An aliquot (4 ml) was removed and added to an ampoule containing the amount of α-(t-butanethiomethyl)styrene (Ia) shown in Table I. The mixture was polymerized at 60° C. for 1 h in the absence of oxygen. The contents of the ampoule were then poured into petroleum spirit (bp 40°–60° C.) and the precipitated polymer was collected and dried in a vacuum oven at 40° C. to constant weight. A small portion was examined by GPC using a Waters Instrument connected to six μ-Styragel columns (10$^6$-, 10$^5$-, 10$^4$-, 10$^3$-, 500- and 100- Å pore size). Tetrahydrofuran was used as eluent at a flow rate of 1 ml/min and the system was calibrated using narrow distribution polystyrene standards (Waters).

TABLE I

| Amount of Ia added (mg) | % conversion | $\overline{M}_n$* |
|---|---|---|
| 0 | 10.9 | 205,190 |
| 9.0 | 10.4 | 46,071 |
| 17.4 | 10.1 | 27,870 |
| 31.4 | 9.4 | 16,795 |
| 1.6 | 8.6 | 9,600 |

*Polystyrene-equivalent number average molecular weight, obtained by GPC

The chain transfer constant calculated from these data was 1.24, which compares favourably with, say, n-butanethiol (chain transfer constant=0.66) or t-butanethiol (chain transfer constant=0.18). These results show that the compound is an efficient chain transfer agent and that the process produces polymers of low molecular weight in a controlled manner. A sample of poly(methyl methacrylate) produced similarly using 298 mg of the chain transfer agent was precipitated two further times from ethyl acetate/petroleum spirit to remove traces of the unreacted chain transfer agent. The resulting polymer of number-average molecular weight 3230 had signals at δ 4.95, and 5.15 ppm in the $^1$H NMR spectrum confirming the presence of the terminal double bond. Integration of the spectrum showed that one of these groups was present per polymer chain. The $^{13}$C NMR spectrum also confirmed the presence of this group.

Example 2

Preparation of Low Molecular Weight Olefin-Terminated Polymers of Styrene Using α-(t-Butanethiomethyl)styrene (Formula I, X=sulphur, $R^1$=phenyl, $R^2$=t-butyl, n=1).

Azobisisobutyronitrile (34.3 mg) was dissolved in freshly distilled styrene (25 ml). Aliquots (5 ml) were removed and added to ampoules containing the amount of α-(t-butanethiomethyl)styrene shown below. The mixtures were polymerized at 60° C. for 3 h in the absence of oxygen. The contents of the ampoules were then poured into methanol and the precipitated polymer was collected and dried and examined by GPC as described above. Samples of polystyrene prepared in this manner using 0 mg, 10.58 mg, 20.12 mg, and 30.73 mg of the chain transfer agent had number-average molecular weights of 125000, 61167, 40466, and 28964, respectively. The chain transfer constant calculated from these data was 0.8, which compares favourably with that of n-butanethiol (chain transfer constant=22) or dodecanethiol (chain transfer constant=15-19). These results show that α-(t-butanethiomethyl)styrene is an efficient chain transfer agent for styrene and that the process produces polymers of low molecular weight in a controlled manner. A sample of polystyrene produced similarly using 320 mg of the chain transfer agent was precipitated two further times from ethyl acetate/methanol to remove traces of the unreacted chain transfer agent. The resulting polymer of number-average molecular weight 3613 had signals at δ 4.7–4.8 and 5.0–5.1 in the $^1$H NMR spectrum confirming the presence of a terminal double bond. Integration of the spectrum showed that one of these groups was present per polymer chain.

Example 3

Preparation of Low Molecular Weight Olefin-Terminated Polymers of Methyl Acrylate Using α-(t-Butanethiomethyl)styrene (Formula I, X=sulphur, $R^1$=phenyl, $R^2$=t-butyl, n=1).

Azobisisobutyronitrile (9.88 mg) was dissolved in freshly distilled methyl acrylate (25 ml). An aliquot (4 ml) was removed and added to an ampoule containing thiophene-free benzene (16 ml) and the amount of α-(t-butanethiomethyl)styrene shown below. The mixture was polymerized at 60° C. for 1 h in the absence of oxygen. The volatiles were then removed and the polymers were dried in vacuo to constant weight and examined by GPC. Samples of poly(methyl acrylate) prepared in this manner using 0 mg, 7.78 mg, 11.67 mg, and 15.55 mg of α-(t-butanethiomethyl)styrene had number-average molecular weights of 496642, 24044, 15963, and 12211, respectively. The chain transfer constant calculated from these data was 3.95. These results show that α-(t-butanethiomethyl)styrene is an efficient chain transfer agent for methyl acrylate and that the process produces polymers of low molecular weight in a controlled manner.

Example 4

Preparation of Low Molecular Weight Olefin-Terminated Polymers of vinyl Acetate Using α-(t-Butanethiomethyl)styrene (Formula I, X=sulphur, $R^1$=phenyl, $R^2$=t-butyl, n=1).

Azobisisobutyronitrile (8.0 mg) was dissolved in freshly distilled vinyl acetate (50 ml). Aliquots (10 ml) were removed and added to ampoules containing the amounts of α-(t-butanethiomethyl)styrene shown below. The mixtures were then polymerized at 60° C. for 1 h in the absence of oxygen. The volatiles were then removed and the polymers were dried in vacuo to constant weight. The polymers were then examined by GPC as described above. Samples of poly(vinyl acetate) prepared in this manner using 0 mg, 6.3 mg, 12.4 mg, and 24.2 mg of α-(t-butanethiomethyl)styrene had number-average molecular weights of 271680, 13869, 7286, and 3976, respectively. The chain transfer constant calculated from these data was 19.9, which is closer to the ideal than that of n-butanethiol (chain transfer constant=48). These results show that α-(t-butanethiomethyl)styrene is an efficient chain transfer agent for vinyl acetate and that the process produces polymers of low molecular weight in a controlled manner.

Example 5

Preparation of Low Molecular Weight Olefin-Terminated Polymers of Methyl Methacrylate Using α-(n-Butanethiomethyl)styrene (Formula I, X=sulphur, $R^1$=phenyl, $R^2$=n-butyl, n=1).

Azobisisobutyronitrile (49.5 mg) was dissolved in freshly distilled methyl methacrylate (25 ml). An aliquot (5 ml) was removed and added to an ampoule containing the amount of α-(n-butanethiomethyl)styrene shown below. The mixture was polymerized at 60° C. for 1 h in the absence of oxygen. The volatiles were then removed and the polymers were dried in vacuo to constant weight. A small portion was examined by GPC as described above. Samples of poly(methyl methacrylate) prepared using 0 mg and 20.4 mg of α-(n-butanethiomethyl)styrene had number-average molecular weights of 280190 and 37405, respectively. The chain transfer constant calculated from these data is 1.10. These results show that α-(n-butanethiomethyl)styrene is an efficient chain transfer agent for methyl methacrylate and that the process produces polymers of low molecular weight.

Example 6

Preparation of Low Molecular Weight Olefin-Terminated Polymers of Styrene Using α-(n-Butanethiomethyl)styrene (Formula I, X=sulphur, $R^1$=phenyl, $R^2$=n-butyl, n=1).

Samples of polystyrene prepared in the manner of example 2 using 0 mg, 19.7 mg, and 39.2 mg of α-(n-butanethiomethyl)styrene had number-average molecular weights of 118140, 45909, and 26922, respectively. The chain transfer constant calculated from these data was 0.68. These results show that α-(n-butanethiomethyl)styrene acts as an efficient chain transfer agent for styrene and that the process produces polymers of low molecular weight.

Example 7

Preparation of Low Molecular Weight α-carboxy, ω-Unsaturated Polymers of Methyl Methacrylate Using α-(Carboxymethanethiomethyl)styrene (Formula I,X-×sulphur, $R^1$=phenyl, $R^2$—$CH_2$ COOH, n=1).

Samples of poly(methyl methacrylate) prepared in the manner of example 5 using 0 mg, 10.0 mg, 20.0 mg, and 40.0 mg of α-(carboxymethanethiomethyl)styrene had number-average molecular weights of 224730, 60531, 31869, and 17728, respectively. The chain transfer constant calculated from these data was 1.30. These results show that α-(carboxymethanethiomethyl)styrene is an efficient chain transfer agent for methyl methacrylate and that the process produces polymers of low molecular weight terminated by a carboxylic acid group. A sample of poly(methylmethacrylate) produced similarly using 300 mg of the chain transfer agent (reaction time 4 h) was precipitated two further times from ethyl acetate/petroleum spirit to remove traces of the unreacted chain transfer agent. The resulting polymer of number-average molecular weight 3291 had signals at δ 4.95 and 5.15 in the $^1$H NMR spectrum confirming the presence of a terminal double bond. Integration of the spectrum showed that there was on average one of these double bonds present per polymer chain.

Example 8;

Preparation of Low Molecular Weight α-Carboxy, ω-Unsaturated Polystyrene Using α-(Carboxymethanethiomethyl)styrene (Formula I, X=sulphur, $R^1$=phenyl, $R^2$=—$CH_2$C00H, n=1).

Samples of polystyrene prepared in the manner of example 2 using 0 mg, 10.0 mg, 20.0 mg, and 30.3 mg of α-(carboxymethanethiomethyl)styrene had number-average molecular weights of 125000, 54700, 33800, and 26300, respectively. The chain transfer constant calculated from these data was 1.00. These results show that α-(carboxymethanethiomethyl)styrene is an efficient chain transfer agent for styrene and that the process produces polymers terminated by a carboxylic acid group of low molecular weight. A sample of polystyrene produced similarly using 500 mg of the chain transfer agent was precipitated two further times from ethyl acetate/methanol to remove traces of the unreacted chain transfer agent. The resulting polymer of number-average molecular weight 2600 had signals at δ 4.7–4.8 and at δ 5.0–5.1 in the $^1$H NMR spectrum confirming the presence of a terminal double bond. Integration of the spectrum showed that one of these groups was present per polymer chain. The infrared spectrum of the polymer showed absorptions at 2500–3000, 1710 and 1300 cm$^{-1}$ confirming the presence of a carboxylic acid group.

Example 9

Preparation of Low Molecular Weight α-Carboxy, ω-Unsaturated Polymers of Styrene Using α-(Carboxyethanethiomethyl)styrene (Formula I, X=sulphur, $R^1$=phenyl, $R^2$=—$CH_2CH_2COOH$, n=1).

Samples of polystyrene prepared in the manner of example 2 using 0 mg, 10.3 mg, 20.2 mg, and 40.3 mg of α-(carboxyethanethiomethyl)styrene had number-average molecular weights of 114340, 56829, 47871, and 30014, respectively. The chain transfer constant calculated from these data was 0.70. These results show that α-(carboxyethanethiomethyl)styrene is an efficient chain transfer agent for styrene and that the process produces polymers terminated by a carboxylic acid group of low molecular weight.

Example 10

Preparation of Low Molecular Weight α-Hydroxy, ω-Unsaturated Poly(methyl methacrylate) Using α-(2-Hydroxyethanethiomethyl)styrene (Formula I, X=sulphur, $R^1$=phenyl, $R^2$=—$CH_2CH_2OH$, n=1).

Samples of poly(methyl methacrylate) prepared in the manner of example 5 using 0 mg, 9.9 mg, 20.1 mg, and 40.0 mg of α-(2-hydroxyethanethiomethyl)styrene had number-average molecular weights of 274490, 56921, 34200, and 17808, respectively. The chain transfer constant calculated from these data was 1.20. These results show that α-(2-hydroxyethanethiomethyl)styrene is an efficient chain transfer agent for methyl methacrylate and that the process produces polymers of low molecular weight terminated by an alcohol group.

Example 11

Preparation of Low Molecular Weight α-Hydroxy, ω-Unsaturated Polymers of Styrene Using α-(2-Hydroxyethanethiomethyl)styrene (Formula I, X=sulphur, $R^1$=phenyl, $R^2$=—$CH_2CH_2OH$, n=1).

Samples of polystyrene prepared in the manner of example 2 using 0 mg, 9.9 mg, 20.1 mg, and 29.9 mg of α-(2-hydroxyethanethiomethyl)styrene had number-average molecular weights of 116570, 57890, 38415, and 28855, respectively. The chain transfer constant calculated from these data was 0.77. These results show that α-(2-hydroxyethanethomethyl)styrene is an efficient chain transfer agent for styrene and that the process produces polymers of low molecular weight terminated by an alcohol group. A sample of polystyrene produced similarly using 201 mg of the chain transfer agent was precipitated two further times from ethyl acetate/methanol to remove traces of the unreacted chain transfer agent. The resulting polymer of number-average molecular weight 6346 had signals at δ 3.35–3.55, 4.7–4.8, and 5.0–5.1 in the $^1$H NMR spectrum confirming the presence of a hydroxymethylene group and a terminal double bond. Integration of the spectrum showed that one each of these groups was present per polymer chain.

Example 12

Preparation of Low Molecular Weight α-Amino, ω-Unsaturated Polymers of Methyl Methacrylate Using α-(2-Aminoethanethiomethyl)styrene (Formula I, X=sulphur, $R^1$=phenyl, $R^2$=—$CH_2CH_2NH_2$, n=1).

Samples of poly(methyl methacrylate) prepared in the manner of example 5 using 0 mg, 11.9 mg, 21.2 mg, and 41.3 mg of α-(2-aminoethanethiomethyl) styrene had number-average molecular weights of 185519, 49427, 32334, and 19065, respectively. The chain transfer constant calculated from these data was 1.05. These results show that α-(2-aminoethanethiomethyl)styrene is an efficient chain transfer agent for methyl methacrylate and that the process produces polymers of low molecular weight terminated by an amine group.

Example 13

Preparation of Low Molecular Weight α-Amino, ω-Unsaturated Polymers of Styrene Using α-(2-Aminoethanethiomethyl)styrene (Formula I, X=sulphur, $R^1$=phenyl, $R^2$=—$CH_2CH_2NH_2$, n=1).

Samples of polystyrene prepared in the manner of example 2 using 0 mg, 10.4 mg, 20.2 mg, and 42.3 mg of α-(2-aminoethanethiomethyl)styrene had number-average molecular weights of 134116, 60766, 39861, and 21920, respectively. The chain transfer constant calculated from these data was 0.79. These results show that α-(2-aminoethanethiomethyl)styrene is an efficient chain transfer agent for styrene and that the process produces polymers of low molecular weight terminated by an amino group. A sample of polystyrene produced similarly using 294 mg of the chain transfer agent was precipitated two further times from toluene/methanol to remove traces of the unreacted chain transfer agent. The resulting polymer of number-average molecular weight 8376 had signals at δ 3.1–3.2, 4.7–4.8, and at 5.0–5.1 in the $^1$H NMR spectrum confirming the presence of the aminomethylene group and a terminal double bond. Integration of the spectrum showed that one of these groups was present per polymer chain.

Example 14

Preparation of Low Molecular Weight α-Trimethoxysilyl, ω-Unsaturated Polymers of Styrene Using α-[3-(Trimethoxysilyl)propanethiomethyl]styrene (Formula I, X=sulphur, $R^1$=phenyl, $R^2$=—$CH_2CH_2CH_2Si(OCH_3)_3$, n=1).

Samples of polystyrene prepared in the manner of example 2 using 0 mg, and 400.7 mg of α-[3-(trimethoxysilyl)propanethiomethyl]styrene had number-average molecular weights of 92287 and 8201, respectively. The chain transfer constant calculated from these data was 0.40. These results show that α-[3-(trimethoxysilyl)propanethiomethyl]styrene is an efficient chain transfer agent for styrene and that the process produces polymers terminated by a trimethoxysilyl group of low molecular weight.

Example 15

Preparation of Low Molecular Weight α-Bromo, ω-Unsaturated Polymers of Methyl Methacrylate Using α-(Bromomethyl)styrene (Formula I, X=Br, $R^1$=phenyl, n=0).

Samples of poly(methyl methacrylate) prepared in the manner of example 5 using 0 mg, 24.96 mg, and 49.30 mg of α-(bromomethyl)styrene had number-average molecular weights of 220453, 16118, and 7863, respectively. The chain transfer constant calculated from these data was 2.27. These results show that α-(bromomethyl)styrene is an efficient chain transfer agent for methyl methacrylate and that the process produces polymers terminated by a bromine end-group of low molecular weight. The sample of poly(methyl methacrylate) with number-average molecular weight 7863 was precipitated two further times from ethyl acetate/petroleum spirit to remove traces of the unreacted chain transfer agent. The resulting polymer had signals at δ 3.60, 5.00, and 5.20 in the $^1$H NMR spectrum confirming the presence of a $BrCH_2$ group and a terminal double bond.

Example 16

Preparation of Low Molecular Weight α-Bromo, ω-Unsaturated Polymers of Styrene Using α-(Bromomethyl)styrene (Formula I, X=Br, $R^1$=phenyl, n=0).

Samples of polystyrene prepared in the manner of example 2 using 0 mg, 15.76 mg, and 27.5 mg of α-(bromomethyl)styrene had number-average molecular weights of 130189, 17024, and 10157, respectively. The chain transfer constant calculated from these data was 2.93. These results show that α-(bromomethyl)styrene is an efficient chain transfer agent for styrene and that the process produces polymers terminated by a bromine end-group of low molecular weight.

Example 17

Preparation of Low Molecular Weight α-Bromo, ω-Unsaturated Polymers of Methyl Acrylate Using α-(Bromomethyl)styrene (Formula I, X=Br, $R^1$=phenyl, n=0).

Samples of poly(methyl acrylate) prepared in the manner of example 3 using 0 mg, 10.57 mg, 15.86 mg, and 21.15 mg of α-(bromomethyl)styrene had number-average molecular weights of 245048, 12675, 7922, and 6549, respectively. The chain transfer constant calculated from these data was 5.25. These results show that α-(bromomethyl)styrene is an efficient chain transfer agent for methyl acrylate and that the process produces polymers of low molecular weight terminated by a bromine end-group.

Example 18

Preparation of Low Molecular Weight Olefin-Terminated Polymers of Methyl Methacrylate Using Ethyl α-(t-Butanethiomethyl)acrylate (Formula I, X=sulphur, $R^1$=—$COOCH_2CH_3$, $R^2$=t-butyl, n=1).

Samples of poly(methyl methacrylate) prepared in the manner of example 5 using 0 mg, 12.2 mg, 22.6 mg, and 43.1 mg of ethyl α-(t-butanethiomethyl)acrylate had a number-average molecular weights of 136696, 61799, 40776, and 24539, respectively. The chain transfer constant calculated from these data was 0.74. These results show that ethyl α-(t-butanethiomethyl)acrylate is an efficient chain transfer agent for methyl methacrylate and that the process produces polymers of low molecular weight in a controlled manner.

Example 19

Preparation of Low Molecular Weight Olefin-Terminated Polymers of Styrene Using Ethyl α-(t-Butanethiomethyl)acrylate (Formula I, X=sulphur, $R^1$=—$COOCH_2CH_3$, $R^2$=t-butyl, n=1).

Samples of polystyrene prepared in the manner of example 2 using 0 mg, 10.3 mg, 21.7 mg, and 40.0 mg of ethyl α-(t-butanethiomethyl)acrylate had number-average molecular weights of 103583, 47806, 30606, and 19359, respectively. The chain transfer constant calculated from these data was 0.95. These results show that ethyl α-(t-butanethiomethyl)acrylate is an efficient chain transfer agent for styrene and that the process produces polymers of low molecular weight in a controlled manner.

Example 20

Preparation of Low Molecular Weight Olefin-Terminated Polymers of Methyl Acrylate Using Ethyl α-(t-Butanethiomethyl)acrylate (Formula I, X=sulphur, $R^1$=—$COOCH_2CH_3$, $R^2$=t-butyl, n=1).

Samples of poly(methyl acrylate) prepared in the manner of example 3 using 0 mg, 5.7 mg, 8.6 mg, and 11.4 mg of ethyl α-(t-butanethiomethyl)acrylate had number-average molecular weights of 842397, 50611, 38942, and 29012, respectively. The chain transfer constant calculated from these data was 2.23. These results show that ethyl α-(t-butanethiomethyl)acrylate is an efficient chain transfer agent for methyl acrylate and that the process produces polymers of low molecular weight in a controlled manner.

Example 21

Preparation of Low Molecular Weight Olefin-Terminated Polymers of Vinyl Acetate Using Ethyl α-(t-Butanethiomethyl)acrylate (Formula I, X=sulphur, $R^1$=—$COOCH_2CH_3$, $R^2$=t-butyl, n=1).

Samples of poly(vinyl acetate) prepared in the manner of example 4 using 4.8 mg, 11.6 mg, and 22.0 mg of ethyl α-(t-butanethiomethyl)acrylate had number-average molecular weights of 61816, 12764, and 1598, respectively. These results show that ethyl α-(t-butanethiomethyl)acrylate acts as a chain transfer agent for vinyl acetate and that the process produces polymers of low molecular weight.

Example 22

Preparation of Low Molecular Weight α-Carboxy, ω-Unsaturated Polymers of Methyl Methacrylate Using Ethyl α-(Carboxymethanethiomethyl)acrylate (Formula I, X=sulphur, $R^1$=—$COOCH_2CH_3$, $R^2$=—$CH_2COOH$, n=1).

Samples of poly(methyl methacrylate) prepared in the manner of example 5 using 0 mg, 9.8 mg, and 21.5 mg of ethyl α-(carboxymethanethiomethyl)acrylate had number-average molecular weights of 164265, 74307, and 44473, respectively. The chain transfer constant calculated from these data was 0.73. These results show that ethyl α-(carboxymethanethiomethyl)acrylate is an efficient chain transfer agent for methyl methacrylate and that the process produces carboxylic acid end-functional polymers of low molecular weight in a controlled manner.

Example 23

Preparation of Low Molecular Weight α-Carboxy, ω-Unsaturated Polymers of Styrene Using Ethyl α-(Carboxymethanethiomethyl)acrylate (Formula I, X=sulphur, $R^1$=—$COOCH_2CH_3$, $R^2$=—$CH_2COOH$, n=1).

Samples of polystyrene prepared in the manner of example 2 using 0 mg, 10.8 mg, 21.0 mg, and 40.2 mg of ethyl α-(carboxymethanethiomethyl)acrylate had number-average molecular weights of 113921, 37477, 20894, and 12076, respectively. The chain transfer constant calculated from these data was 1.72. These results show that ethyl α-(carboxymethanethiomethyl)acrylate is an efficient chain transfer agent for styrene and that the process produces carboxylic acid end-functional polymers of low molecular weight in a controlled manner. A sample of polystyrene produced similarly using 186 mg of the chain transfer agent was precipitated two further times from toluene/methanol to remove traces of the unreacted chain transfer agent. The resulting polymer of number-average molecular weight 4014 had signals at δ 1.15, 3.9–4.1, 5.0–5.1, and 5.8–5.9 in the $^1$H NMR spectrum confirming the presence of an ethyl ester and a terminal double bond. Integration of the spectrum showed that one each of these groups was present per polymer chain. The infrared spectrum of the polymer showed absorptions at 3500−2300 (broad), 1705 (broad) and 1295 cm$^{-1}$ consistent with the presence of a carboxylic acid group.

Example 24

Preparation of Low Molecular Weight α,ω-Dicarboxy, ω-Unsaturated Polymers of Methyl Methacrylate Using α-(Carboxymethanethiomethyl)acrylic Acid (Formula I, X=sulphur, R$^1$=—COOH, R$^2$=—CH$_2$COOH, n=1).

Samples of poly(methyl methacrylate) prepared in the manner of example 5 using 0 mg, 10.0 mg, 20.2 mg, and 40.0 mg of α-(carboxymethanethiomethyl)acrylic acid had number-average molecular weights of 154487, 69520, 40763, and 24084, respectively. The chain transfer constant calculated from these data was 0.74. These results show that α-(carboxymethanethiomethyl)acrylic acid is an efficient chain transfer agent for methyl methacrylate and that the process produces low molecular weight polymers having carboxylic acid groups at both ends.

Example 25

Preparation of Low Molecular Weight α,ω-Dicarboxy, α-Unsaturated Polymers of Styrene Using α-(Carboxymethanethiomethyl)acrylic Acid (Formula I, X=sulphur, R$^1$=—COOH, R$^2$=—CH$_2$COOH, n=1).

Azobisisobutyronitrile (34.3 mg) was dissolved in freshly distilled styrene (25 ml). Acetone (25 ml) was added to ensure that the chain transfer agent was soluble. Aliquots (10 ml) were removed and added to ampoules containing the amount of the chain transfer agent shown below. The mixtures were polymerized and examined as per example 2. Samples of polystyrene prepared using 0 mg, 10.1 mg, 20.3 mg, and 40.2 mg of α-(carboxymethanethiomethyl)acrylic acid had number-average molecular weights of 53361, 28162, 19652, and 12118, respectively. The chain transfer constant calculated from these data was 1.27. These results show that α-(carboxymethanethiomethyl)acrylic acid is an efficient chain transfer agent for styrene and that the process produces low molecular weight polymers having a carboxylic acid group at both ends. The polymer of number-average molecular weight 12118, was precipitated two further times from toluene/methanol to remove traces of the chain transfer agent. The IR spectrum showed absorptions at 1735 and at 1700 cm$^{-1}$ confirming the presence of the saturated and α,β-unsaturated carboxylic acid groups at the ends of the polymer chain.

Example 26

Preparation of Low Molecular Weight Olefin-Terminated Polymers of Methyl Methacrylate Using α-(t-Butanethiomethyl)acrylonitrile (Formula I, X=sulphur, R$^1$=—CN, R$^2$=t-butyl, n=1).

Samples of poly(methyl methacrylate) prepared in the manner of example 5 using 0 mg, 10.5 mg, 19.9 mg, and 38.3 mg of α-(t-butanethiomethyl)acrylonitrile had number-average molecular weights of 181352, 35500, 23769, and 12724, respectively. The chain transfer constant calculated from these data was 1.36. These results show that α-(t-butanethiomethyl)acrylonitrile is an efficient chain transfer agent for methyl methacrylate and that the process produces polymers of low molecular weight in a controlled manner.

Example 27

Preparation of Low Molecular Weight Olefin-Terminated Polymers of Styrene Using α-(t-Butanethiomethyl)acrylonitrile (Formula I, X=sulphur, R$^1$=—CN, R$^2$=t-butyl, n=1).

Samples of polystyrene prepared in the manner of example 2 using 0 mg, 10.5 mg, and 30.6 mg of α-(t-butanethiomethyl)acrylonitrile had number-average molecular weights of 118703, 29783, and 11747, respectively. The chain transfer constant calculated from these data was 1.75. These results show that α-(t-butanethiomethyl)acrylonitrile is an efficient chain transfer agent for styrene and that the process produces polymers of low molecular weight in a controlled manner. A sample of polystyrene produced similarly using 200 mg of the chain transfer agent was precipitated two further times from ethyl acetate/methanol to remove traces of the unreacted chain transfer agent. The resulting polymer of number-average molecular weight 5491 had signals at δ 5.3–5.4 in the $^1$H NMR spectrum confirming the presence of a terminal double bond. Integration of the spectrum showed that one of these groups was present per polymer chain. The infrared spectrum of the polymer showed an absorption of 2220 cm$^{-1}$ confirming the presence of a cyano group.

Example 28

Preparation of Low Molecular Weight Olefin-Terminated Polymers of Methyl Acrylate Using α-(t-Butanethiomethyl)acrylonitrile (Formula I, X=sulphur, R$^1$=—CN, R$^2$=t-butyl, n=1).

Samples of poly(methyl acrylate) prepared in the manner of example 3 using 0 mg, 8.0 mg, 12.1 mg, and 16.1 mg of α-(t-butanethiomethyl)acrylonitrile had number-average molecular weights of 224288, 37084, 26347, and 21079, respectively. The chain transfer constant calculated from these data was 1.64. These results show that α-(t-butanethiomethyl)acrylonitrile is an efficient chain transfer agent for methyl acrylate and that the process produces polymers of low molecular weight in a controlled manner.

Example 29

Preparation of Low Molecular Weight Olefin-Terminated Polymers of Vinyl Acetate Using α-(t-Butanethiomethyl)acrylonitrile (Formula I, X=sulphur, R$^1$=CN, R$^2$=t-butyl, n=1).

Samples of poly(vinyl acetate) prepared in the manner of example 4 using 0 mg, 5.6 mg, 10.7 mg, and 22.1 mg of α-(t-butanethiomethyl)acrylonitrile had number-average molecular weights of 243721, 10438, 2905, and 1079, respectively. The chain transfer constant calculated from these data was 60. These results show that α-(t-butanethiomethyl)acrylonitrile acts as a chain transfer agent for vinyl acetate and that the process produces polymers of low molecular weight.

Example 30

Preparation of Low Molecular Weight α-Bromo, ω-Unsaturated Polymers of Methyl Methacrylate Using Ethyl α-(Bromomethyl)acrylate (Formula I, X=Br, $R^1$=—COOCH$_2$CH$_3$, n=0).

Samples of poly(methyl methacrylate) prepared in the manner of example 5 using 0 mg, 26.62 mg, and 51.33 mg of ethyl α-(bromomethyl)acrylate had number-average molecular weights of 220453, 20690, and 11668, respectively. The chain transfer constant calculated from these data was 1.45. These results show that ethyl α-(bromomethyl)acrylate is an efficient chain transfer agent for methyl methacrylate and that the process produces bromine end-functional polymers of low molecular weight in a controlled manner.

Example 31

Preparation of Low Molecular Weight α-Bromo, ω-Unsaturated Polymers of Methyl Acrylate Using Ethyl α-(Bromomethyl)acrylate (Formula I, X=Br, $R^1$=—COOCH$_2$CH$_3$, n=0).

Samples of poly(methyl acrylate) prepared in the manner of example 3 using 0 mg and 31.3 mg of ethyl α-(bromomethyl)acrylate had number-average molecular weights of 496642 and 9888, respectively. The chain transfer constant calculated from these data was 2.33. These results show that ethyl α-(bromomethyl)acrylate is an efficient chain transfer agent for methyl acrylate and that the process produces polymers of low molecular weight.

Example 32

Preparation of Low Molecular Weight Olefin-Terminated Polymers of Methyl Methacrylate Using α-(Diethyoxyphosphorylmethyl)styrene (Formula I, X=P(O), $R^1$=phenyl, $R^2$=ethoxy, n=2).

Samples of poly(methyl methacrylate) prepared in the manner of example 5 using 0 mg, 11.4 mg, 22.6 mg, and 43.8 mg of α-(diethoxyphosphorylmethyl)styrene had number-average molecular weights of 210866, 124132, 88457, and 63441, respectively. The chain transfer constant calculated from these data was 0.35. These results show that α-(diethoxyphosphorylmethyl)styrene is an efficient chain transfer agent for methyl methacrylate and that the process produces polymers of low molecular weight in a controlled manner.

Example 33

Preparation of Low Molecular Weight Olefin-Terminated Polymers of Methyl Methacrylate Using Ethyl α-(Trimethylsilylmethyl)acrylate (Formula I, X=Si, $R^1$=—COOCH$_2$CH$_3$, $R^2$=methyl, n=3).

Samples of poly(methyl methacrylate) prepared in the manner of example 5using 0 mg and 19.4 mg of ethyl α-(trimethlsilylmethyl)acrylate had number-average molecular weights of 181352 and 137986, respectively. The chain transfer constant calculated from these data was 0.08. These results show that ethyl α-(trimethylsilylmethyl)acrylate acts as a chain transfer agent for methyl methacrylate and that the process produces polymers of lowered molecular weight.

Example 34

Preparation of Low Molecular Weight Olefin-Terminated Polymers of Methyl Methacrylate Using Ethyl α-(Tri-n-butylstannylmethyl)acrylate (Formula I, X=Sn, $R^1$=—COOCh$_2$Ch$_3$, $R^2$=n-butyl, n=3).

Samples of poly(methyl methacrylate) prepared in the manner of example 5 using 0 mg, 12.6 mg, 23.0 mg, and 37.7 mg of ethyl α-(tri-n-butylstannylmethyl)acrylate had number-average molecular weights of 196981, 36232, 22349, and 15473, respectively. The chain transfer constant calculated from these data was 3.01. These results show that ethyl α-(tri-n-butylstannylmethyl)acrylate is an efficient chain transfer agent for methyl methacrylate and that the process produces polymers of low melecular weight in a controlled manner.

Example 35

Preparation of Low Molecular Weight Olefin-Terminated Polymers of Methyl Methacrylate Using Ethyl α-(Benzenesulphonylmethyl)acrylate (Formula I, X=S(O)$_2$, $R^1$=—COOCH$_2$CH$_3$, $R^2$=phenyl, n=1).

Samples of poly(methyl methacrylate) prepared in the manner of example 5using 0 mg, 10.3 mg, 20.1 mg, and 30.0 mg of ethyl α-(benzenesulphonylmethyl)acrylate had number-average molecular weights of 181352, 64607, 38949, and 29612, respectively. The chain transfer constant calculated from these data was 1.14. These results show that ethyl α-(benzenesulphonylmethyl)acrylate is an efficient chain transfer agent for methyl methacrylate and that the process produces polymers of low melecular weight in a controlled manner.

Example 36

Preparation of Low Molecular Weight Olefin-Terminated Polymers of Styrene Using Ethyl α-(Benzenesulphonylmethyl)acrylate (Formula I, X=S(O)$_2$, $R^1$=—COOCH$_2$CH$_3$, $R^2$=phenyl, n=1).

Samples of polystyrene prepared in the manner of example 2 using 0 mg, 10.9 mg, 20.4 mg, and 40.1 mg of ethyl α-(benzenesulphonylmethyl)acrylate had number-average molecular weights of 112707, 15520, 9099, and 4728, respectively. The chain transfer constant calculated from these data was 5.75. These results show that ethyl α-(benzenesulphonylmethyl)acrylate is an efficient chain transfer agent for styrene and that the process produces polymers of low molecular weight in a controlled manner. The sample of polystyrene of number-average molecular weight 4728 was precipitated two further times from ethyl acetate/methanol to remove traces of the unreacted chain transfer agent. The resulting polymer had signals at δ 5.0–5.1, and 5.8–5.9 in the $^1$H NMR spectrum confirming the presence of the terminal double bond.

Example 37

Preparation of Low Molecular Weight Olefin-Terminated Polymers of Methyl Methacrylate Using δ-(n-Butanesulphinylmethyl)styrene (Formula I, X=S(O), $R^1$=phenyl, $R^2$=n-butyl, n=1).

Samples of poly(methyl methacrylate) prepared in the manner of example 5 using 0 mg, 10.2 mg, and 20.3 mg of ethyl α-(n-butanesulphinylmethyl)styrene had number-average molecular weights of 236818, 40155, and 24323, respectively. The chain transfer constant calculated from these data was 1.89. These results show that ethyl α-(n-butanesulphinylmethyl)styrene is an efficient chain transfer agent for methyl methacrylate and that the process produces polymers of low molecular weight.

Example 38

Preparation of Low Molecular Weight Olefin-Terminated Polymers of Methyl Methacrylate Using α-(Benzenesulphonylmethyl)vinyl Acetate (Formula I, X=S(O)$_2$, R$^1$=—OAc, R$^2$=phenyl, n=1)

Samples of poly(methyl methacrylate) prepared in the manner of example 5 using 0 mg, 27.3 mg, 49.0 mg, and 100.8 mg of α-(benzenesulphonylmethyl)vinyl acetate had number-average molecular weights of 269320, 194204, 163144, and 104847, respectively. The chain transfer constant calculated from these data was 0.065. These results show that α-(benzenesulphonylmethyl)vinyl acetate acts as a chain transfer agent for methyl methacrylate and that the process produces polymers of low molecular weight in a controlled manner.

Example 39

Preparation of Low Molecular Weight Olefin-Terminated Polymers of Styrene Using α-(Benzenesulphonylmethyl)vinyl Acetate (Formula I, X=S(O)$_2$, R$^1$=—OAc, R$^2$=phenyl, n=1)

Samples of polystyrene prepared in the manner of example 2 using 0 mg, 20.0 mg, 40.0 mg, and 80.4 mg of α-(benzenesulphonylmethyl)vinyl acetate had number-average molecular weights of 105213, 102276, 97437, and 89049, respectively. The chain transfer constant calculated from these data was 0.02. These results show that α-(benzenesulphonylmethyl)vinyl acetate acts as a chain transfer agent for styrene and that the process produces polymers of low molecular weight in a controlled manner.

Example 40

Preparation of Low Molecular Weight Olefin-Terminated Polymers of Methyl Acrylate Using α-(Benzenesulphonylmethyl)vinyl Acetate (Formula I, X=S(O)$_2$, R$^1$=—OAc, R$^2$=phenyl, n=1)

Samples of poly(methyl acrylate) prepared in the manner of example 3 using 22.8 mg, 50.0 mg, and 99.4 mg of α-(benzenesulphonylmethyl)vinyl acetate had number-average molecular weights of 107713, 73613, and 40108, respectively. The chain transfer constant calculated from these data was 0.20. These results show that α-(benzenesulphonylmethyl)vinyl acetate is an efficient chain transfer agent for methyl acrylate and that the process produces polymers of low molecular weight in a controlled manner.

Example 41

Preparation of Low Molecular Weight Olefin-Terminated Polymers of Vinyl Acetate Using α-(Benzenesulphonylmethyl)vinyl Acetate (Formula I, X=S(O)$_2$, R$^1$=—OAc, R$^2$=phenyl, n=1)

Samples of poly(vinyl acetate) prepared in the manner of example 4 using 0 mg, 5.1 mg, 10.3 mg, and 20.5 mg of α-(benzenesulphonylmethyl)vinyl acetate had number-average molecular weights of 144664, 113338, 64712, and 39212, respectively. The chain transfer constant calculated from these data was 2.8. These results show that α-(benzenesulphonylmethyl)vinyl acetate is an efficient chain transfer agent for vinyl acetate and that the process produces polymers of low molecular weight in a controlled manner.

Example 42

Preparation of Low Molecular Weight α-Bromo, ω-Unsaturated Polymers of Methyl Methacrylate Using α-(Bromomethyl)acrylonitrile (Formula I, X=Br, R$^1$=—CN, n=0)

Samples of poly(methyl methacrylate) prepared in the manner of example 5 using 0 mg, 24.0 mg, 49.0 mg, and 99.8 mg of α-(bromomethyl)acrylonitrile had number-average molecular weights of 234433, 10029, 5263, and 3124, respectively. The chain transfer constant calculated from these data was 2.22. These results show that α-(bromomethyl)acrylonitrile is an efficient chain transfer agent for methyl methacrylate and that the process produces polymers of low molecular weight in a controlled manner.

Example 43

Preparation of Low Molecular Weight α-Bromo, ω-Unsaturated Polymers of Methyl Acrylate Using α-(Bromomethyl)acrylonitrile (Formula I, X=Br, R$^1$=—CN, n=0)

Samples of poly(methyl acrylate) prepared in the manner of example 5 using 22.8 mg, 50.0 mg, and 99.4 mg of α-(bromomethyl)acrylonitrile had number-average molecular weights of 107713, 73613, and 40108, respectively. The chain transfer constant calculated from these data was 3.0. These results show that α-(bromomethyl)acrylonitrile is an efficient chain transfer agent for methyl acrylate and that the process produces polymers of low molecular weight in a controlled manner.

Example 44

Preparation of Low Molecular Weight α-Chloro, ω-Unsaturated Polymers of Methyl Acrylate Using α-(Chloromethyl)acrylonitrile (Formula I, X=Cl, R$^1$=—CN, n=0)

Samples of poly(methyl acrylate) prepared in the manner of example 3 using 0 mg, 11.8 mg, 24.8 mg, and 50.8 mg of α-(chloromethyl)acrylonitrile had number-average molecular weights of 502537, 232619, 158821, and 74136, respectively. The chain transfer constant calculated from these data was 0.05. These results show that α-(chloromethyl)acrylonitrile acts as a chain transfer agent for methyl acrylate and that the process produces polymers of low molecular weight in a controlled manner.

Example 45

Preparation of Low Molecular Weight Polyacrylonitrile Using α-(t-Butanethiomethyl)acrylonitrile (Formula I, X=sulphur, R$^1$=—CN, R$^2$=t-butyl, n=1).

Azobisisobutyronitrile (7.4 mg) was dissolved in freshly distilled acrylonitrile (10 ml). An aliquot (2 ml) was removed and added to α-(t-butanethiomethyl)acrylonitrile (14.5 mg) and the mixture was polymerized in the absence of oxygen for 1 h at 60° C. The resulting polymer was precipitated in toluene. A portion (100 mg) of the dried polymer was dissolved in dimethylformamide (10 ml) and the viscosity was measured using a Gardiner Bubble viscometer. The resulting polymer had a viscosity less than that of tube B. A similar polymer prepared without added chain transfer agent had a viscosity equal to that of tube E. This result shows that the polymer prepared using α-(t-butanethiomethyl)acrylonitrile had a lower molecular weight than that prepared without, and that α-(t-butanethiomethyl)a- crylonitrile acts as a chain transfer agent for acrylonitrile.

Example 46

Preparation of Low Molecular Weight Polyacrylonitrile Using α-(t-Butanethiomethyl)styrene (Formula I, X=sulphur, $R^1$=phenyl, $R^2$=t-butyl, n=1).

A polymer prepared as above (Example 45) using α-(t-butanethiomethyl)-styrene (15.6 mg) was precipitated in toluene. A portion (100 mg) of the dried polymer was dissolved in dimethylformamide (10 ml) and the viscosity was measured using a Gardiner Bubble viscometer. The resulting polymer had a viscosity less than that of tube B. A similar polymer prepared without added chain transfer agent had a viscosity equal to that of tube E. This result shows that the polymer prepared using α-(t-butanethiomethyl)styrene had a lower molecular weight than that prepared without, and that α-(t-butanethiomethyl)styrene acts as a chain transfer agent for acrylonitrile.

Example 47

Preparation of Low Molecular Weight Polymers of Methyl Methacrylate (MMA) Using α-Benzyloxystyrene (Formula II, $R^1$=phenyl, $R^2$=benzyl).

Azobisisobutyronitrile (19.4 mg) was dissolved in freshly distilled methyl methacrylate (10.00 ml). An aliquot (2.00 ml) was removed and added to an ampoule containing the amount of the chain transfer agent, α-benzyloxystyrene, shown in Table II. The mixture was polymerized at 60° C. for 1 h in the absense of oxygen. The contents of the ampoule were then poured into pentane and the precipitated polymer was collected and dried in vacuo to constant weight. A small portion was examined by GPC using a Waters Instrument connected to six μ-Styragel columns ($10^6$-, $10^5$-, $10^4$-, $10^3$-, 500- and 100- Å pore size). Tetrahydrofuran was used as eluent and the system was calibrated using narrow distribution polystyrene standards (Waters).

TABLE II

| α-Benzyloxystyrene added (mg) | [α-Benzyloxystyrene] / [Methyl Methacrylate] | $\overline{M}_n$* | % Conversion |
| --- | --- | --- | --- |
| 0 | 0 | 207,000 | 11.8 |
| 4.0 | $1.02 \times 10^{-3}$ | 96,564 | 12.2 |
| 10.3 | $2.62 \times 10^{-3}$ | 41,395 | 10.1 |
| 15.8 | $4.02 \times 10^{-3}$ | 28,123 | 11.0 |
| 22.0 | $5.60 \times 10^{-3}$ | 21,275 | 10.7 |
| 25.3 | $6.44 \times 10^{-3}$ | 18,688 | 10.6 |
| 37.0 | $9.42 \times 10^{-3}$ | 13,397 | 10.0 |
| 41.0 | $1.04 \times 10^{-2}$ | 11,849 | 12.1 |
| 48.0 | $1.22 \times 10^{-2}$ | 10,380 | 10.0 |

*Polystyrene-equivalent number-average molecular weight, obtained by GPC.

The chain transfer constant calculated from these data was 0.76, which compares favourably with that from n-butanethiol (chain transfer constant=0.66). These results show that α-benzyloxystyrene is an efficient chain transfer agent for methyl methacrylate and that the process produces polymers of low molecular weight in a controlled manner.

Example 48

Preparation of Low Molecular Weight Polymers of Styrene Using α-Benzyloxystyrene (Formula II, $R^1$=phenyl, $R^2$=benzyl).

Azobisisobutyronitrile (70.4 mg) was added to freshly distilled styrene (50 ml). An aliquot (10 ml) of this mixture was removed and added to an ampoule containing the amount of benzyloxystyrene shown (Table III). The mixture was polymerized for 1 h at 60° C. in the absence of oxygen. The contents of the ampoule were then poured into methanol (110 ml) and the precipitated polymer was collected, dried and examined by GPC as described previously.

TABLE III

| α-Benzyloxystyrene added (mg) | [α-Benzyloxystyrene] / [Styrene] | $\overline{M}_n$* | % Conversion |
| --- | --- | --- | --- |
| 0.0 | 0.00 | 137,320 | 2.8 |
| 44.5 | $2.43 \times 10^{-3}$ | 78,812 | 3.2 |
| 45.6 | $2.49 \times 10^{-3}$ | 78,010 | 2.9 |
| 49.1 | $2.68 \times 10^{-3}$ | 76,022 | 3.0 |
| 91.6 | $5.00 \times 10^{-3}$ | 50,674 | 2.4 |
| 144.9 | $7.91 \times 10^{-3}$ | 38,146 | 3.0 |
| 170.3 | $9.29 \times 10^{-3}$ | 32,928 | 3.4 |
| 231.4 | $1.26 \times 10^{-2}$ | 26,802 | 3.0 |
| 261.5 | $1.43 \times 10^{-2}$ | 23,417 | 3.5 |

The chain transfer constant calculated from these data was 0.26, which is closer to the ideal than that from n-butanethiol (chain transfer constant=22). These results show that α-benzyloxystyrene is an efficient chain transfer agent for styrene and that the process produces polymers of low molecular weight in a controlled manner.

Example 49

Preparation of Low Molecular Weight Polymers of Methyl Acrylate Using α-Benzyloxystyrene (Formula II, $R^1$=phenyl, $R^2$=benzyl).

Azobisisobutyronitrile (9.1 mg) was dissolved in a mixture of thiophenefree benzene (80 ml) and freshly distilled methyl acrylate (20 ml). Aliquots (10 ml) were removed and added to ampoules containing the amounts of α-benzyloxystyrene shown below. The mixtures were then polymerized at 60° C. for 1 h in the absence of oxygen. The volatiles were then removed and the polymers were dried in vacuo to constant weight. The polymers were then examined by GPC as described above. Samples of poly(methyl acrylate) prepared in this manner using 0 mg, 4.8 mg, and 10.2 mg of α-benzyloxystyrene had number-average molecular weights of 577200, 14652, and 6866, respectively. The chain transfer constant calculated from these data was 5.7. These results show that α-benzyloxystyrene is an efficient chain transfer agent for methyl acrylate and that the process produces polymers of low molecular weight in a controlled manner.

Example 50

Preparation of Low Molecular Weight Polymers of Vinyl Acetate Using α-Benzyloxystyrene (Formula II, $R^1$=phenyl, $R^2$=benzyl).

Azobisisobutyronitrile (8.0 mg) was dissolved in freshly distilled vinyl acetate (50 ml). Aliquots (10 ml) were removed and added to ampoules containing the amounts of α-benzyloxystyrene shown below. The mixtures were then polymerized at 60° C. for 1 h in the absence of oxygen. The volatiles were then removed and the polymers were dried in vacuo to constant weight. The polymers were then examined by GPC as described above. Samples of poly(vinyl acetate) prepared in this manner using 0 mg, 2.3 mg, 5.1 mg, 10.0 mg, and 20.7 mg of α-benzyloxystyrene had number-average molecular weights of 260760, 75723, 35337, 22116, and 9458, respectively. The chain transfer constant calculated from these data was 9.7, which is closer to the ideal than that of n-butanethiol (chain transfer constant =48). These results show that α-benzyloxystyrene is an efficient chain transfer agent for vinyl acetate and that the process produces polymers of low molecular weight in a controlled manner.

Example 51

Preparation of Low Molecular Weight Polymers of Methyl Methacrylate Using α-Benzyloxyacrylonitrile (Formula II, $R^1$=—CN, $R^2$=benzyl).

Azobisisobutyronitrile (19.4 mg) was dissolved in freshly distilled methyl methacrylate (10 ml). Aliquots (2 ml) were removed and added to ampoules containing the amounts of α-benzyloxyacrylonitrile shown below. The mixtures were then polymerized at 60° C. for 1 h in the absence of oxygen. The contents of the ampoules were added to separate portions of petroleum spirit (30 ml) and the preciptiated polymers were collected and dried in vacuo to constant weight. The polymers were then examined by GPC as described above. Samples of poly(methyl methacrylate) prepared in this manner using 0 mg, 10.0 mg, 12.4 mg, and 34.7 mg of α-benzyloxyacrylonitrile had number-average molecular weights of 200810, 132040, 124140, and 69706, respectively. The chain transfer constant calculated from these data was 0.082. These results show that α-benzyloxyacrylonitrile acts as a chain transfer agent for methyl methacrylate and that the process produces polymers of lower molecular weight in a controlled manner.

Example 52

Preparation of Low Molecular Weight Polymers of Styrene Using α-Benzyloxyacrylonitrile (Formula II, $R^1$=—CN, $R^2$=benzyl).

Samples of polystyrene prepared in the manner of example 48 using 42.8 mg, 86.4 mg, and 153.2 mg of α-benzyloxyacrylonitrile had number-average molecular weights of 107460, 95028, and 83280, respectively. The chain transfer constant calculated from these data was 0.038. These results show that α-benzyloxyacrylonitrile acts as a chain transfer agent for styrene and that the process produces polymers of controlled molecular weight.

Example 53

Preparation of Low Molecular Weight Polymers of Methyl Acrylate Using α-Benzyloxyacrylonitrile (Formula II, $R^1$=—CN, $R^2$=benzyl).

Samples of poly(methyl acrylate) prepared in the manner of example 49 using 0 mg, 10.4 mg, 40.0 mg, and 66.6 mg of α-benzyloxyacrylonitrile had number-average molecular weights of 500000, 75781, 23038, and 14779, respectively. The chain transfer constant calculated from these data was 0.30. These results show that α-benzyloxyacrylonitrile acts as an efficient chain transfer agent for methyl acrylate and that the process produces polymers of low molecular weight in a controlled manner.

Example 54

Preparation of Low Molecular Weight Polymers of Vinyl Acetate Using α-Benzyloxyacrylonitrile (Formula II, $R^1$=—CN, $R^2$=benzyl).

Samples of poly(vinyl acetate) prepared in the manner of example 50 using 0 mg, 2.0 mg, and 2.0 mg of α-benzyloxyacrylonitrile had number-average molecular weights of 225319, 46036, and 6032, respectively. The chain transfer constant calculated from these data was 11. These results show that α-benzyloxyacrylonitrile acts as an efficient chain transfer agent for vinyl acetate and that the process produces polymers of low molecular weight in a controlled manner.

Example 55

Preparation of Low Molecular Weight Polymers of Methyl Methacrylate Using Methyl α-Benzyloxyacrylate (Formula II, $R^1$=COOCH$_3$, $R^2$=benzyl).

Samples of poly(methyl methacrylate) prepared in the manner of example 47 using 7.9 mg, 16.3 mg, 26.3 mg, and 40.1 mg of methyl α-benzyloxyacrylate had number-average molecular weights of 99822, 73462, 55557, and 41633, respectively. The chain transfer constant calculated from these data was 0.16. These results show that methyl α-benzyloxyacrylate acts as a chain transfer agent for methyl methacrylate and that the process produces polymers of low molecular weight in a controlled manner.

Example 56

Preparation of Low Molecular Weight Polymers of Styrene. Using Methyl α-Benzyloxyacrylate (Formula II, $R^1$=COOCH$_3$, $R^2$=benzyl).

Samples of polystyrene prepared in the manner of example 48 using 0 mg, 20.2 mg, and 80.4 mg of methyl α-benzyloxyacrylate had number-average molecular weights of 106391, 92060, and 71658, respectively. The chain transfer constant calculated from these data was 0.042. These results show that methyl α-benzyloxyacrylate acts as a chain transfer agent for styrene and that the process produces polymers of lower molecular weight.

Example 57

Preparation of Low Molecular Weight Polymers of Methyl Acrylate Using Methyl α-Benzyloxyacrylate (Formula II, $R^1$=—COOCH$_3$, $R^2$=benzyl).

Samples of methyl acrylate prepared in the manner of example 49 using 0 mg, 10.1 mg, 25.0 mg, and 60.2 mg of methyl α-benzyloxyacrylate had number-average molecular weights of 442463, 41424, 18894, and 8964, respectively. The chain transfer constant calculated from these data was 0.56. These results show that methyl α-benzyloxyacrylate acts as an efficient chain transfer agent for methyl acrylate and that the process produces polymers of low molecular weight in a controlled manner.

Example 58

Preparation of Low Molecular Weight Polymers of Vinyl Acetate Using Methyl α-Benzyloxyacrylate (Formula II, $R^1$=—COOCH$_3$, $R^2$=benzyl).

Samples of poly(vinyl acetate) prepared in the manner of example 50 using 0 mg, 4.8 mg, 10.1 mg, and 20.2 mg of methyl α-benzyloxyacrylate had number-average molecular weights of 245714, 17851, 8382, and 4252, respectively. The chain transfer constant calculated from these data was 20.8. These results show that methyl α-benzyloxyacrylate acts as a chain transfer agent for vinyl acetate and that the process produces polymers of low molecular weight in a controlled manner.

Example 59

Preparation of Low Molecular Weight Polymers of Methyl Methacrylate Using α-Benzyloxyacrylamide (Formula II, $R^1$=—CONH$_2$, $R^2$=benzyl).

Samples of poly(methyl methacrylate) prepared in the manner of example 47 using 7.3 mg, 15.2 mg, 25.3 mg, and 40.3 mg of α-benzyloxyacrylamide had number-average molecular weights of 57642, 36026, 23419, and 15687, respectively. The chain transfer constant calculated from these data was 0.47. These results show that α-benzyloxyacrylamide acts as an efficient chain transfer agent for methyl methacrylate and that the process produces polymers of low molecular weight in a controlled manner.

Example 60

Preparation of Low Molecular Weight Polymers of Styrene Using α-Benzyloxyacrylamide (Formula II, $R^1$=—$CONH_2$, $R^2$=benzyl).

Samples of polystyrene prepared in the manner of example 48 using 0 mg, 20.1 mg, 39.6 mg, and 80.6 mg of α-benzyloxyacrylamide had number-average molecular weights of 66537, 48539, 42313, and 33687, respectively. The chain transfer constant calculated from these data was 0.13. These results show that α-benzyloxyacrylamide acts as a chain transfer agent for styrene and that the process produces polymers of low molecular weight in a controlled manner.

Example 61

Preparation of Low Molecular Weight Polymers of Methyl Acrylate Using α-Benzyloxyacrylamide (Formula II, $R^1$=—$CONH_2$, $R^2$=benzyl).

Samples of poly(methyl acrylate) prepared in the manner of example 49 using 0 mg, 9.8 mg, 24.7 mg, and 58.2 mg of α-benzyloxyacrylamide had number-average molecular weights of 529892, 26913, 11193, and 5431, respectively. The chain transfer constant calculated from these data was 1.10. These results show that α-benzyloxyacrylamide acts as an efficient chain transfer agent for methyl acrylate and that the process produces polymers of low molecular weight in a controlled manner.

Example 62

Preparation of Low Molecular Weight Olefin-Terminated Polymers of Methyl Methacrylate Using α-Allyloxystyrene (Formula II; $R^1$=phenyl, $R^2$=allyl).

Samples of poly(methyl methacrylate) prepared in the manner of example 47 using 0 mg, 14.6 mg, and 30.1 mg of α-allyloxystyrene had number-average molecular weights of 238380, 28873, and 14953, respectively. The chain transfer constant calculated from these data was 0.62. These results show that α-allyloxystyrene acts as an efficient chain transfer agent for methyl methacrylate and that the process produces polymers of low molecular weight. A sample of poly(methyl methacrylate) produced similarly using 294 mg of α-allyloxystyrene was precipitated two further times from ethyl acetate/pentane to remove traces of the unreacted chain transfer agent. The resulting polymer of number-average molecular weight 2418 had signals at δ 4.8–5.0 and at δ 5.5–5.8 in the $^1$H NMR spectrum confirming the presence of a terminal double bond. Integration of the spectrum showed that one of these groups was present per polymer chain.

Example 63

Preparation of Low Molecular Weight Olefin-Terminated Polymers of Styrene Using α-Allyloxystyrene (Formula II, $R^1$=phenyl, $R^2$=allyl).

Samples of polystyrene prepared in the manner of example 48 using 0 mg, 97.0 mg, and 197.0 mg of α-allyloxystyrene had number-average molecular weights of 137320, 53106, and 31889, respectively. The chain transfer constant calculated from these data was 0.18. These results show that α-allyloxystyrene acts as an efficient chain transfer agent for styrene and that the process produces polymers of low molecular weight in a controlled manner.

Example 64

Preparation of Low Molecular Weight Polymers of Methyl Methacrylate Using α-Isopropyloxystyrene (Formula II, $R^1$=phenyl, $R^2$=isopropyl).

Samples of poly(methyl methacrylate) prepared in the manner of example 47 using 0 mg, 20.5 mg, and 39.1 mg of α-isopropyloxystyrene had number-average molecular weights of 247208, 48601, and 26986, respectively. The chain transfer constant calculated from these data was 0.25. These results show that α-isopropyloxystyrene acts as a chain transfer agent for methyl methacrylate and that the process produces polymers of low molecular weight in a controlled manner.

Example 65

Preparation of Low Molecular Weight Polymers of Methyl Methacrylate Using α-Methoxystyrene (Formula II, $R^1$=phenyl, $R^2$=methyl).

Samples of poly(methyl methacrylate) prepared in the manner of example 47 using 0 mg, 17.0 mg, and 32.4 mg of α-methoxystyrene had number-average molecular weights of 240673, 198460, and 151800, respectively. The chain transfer constant calculated from these data was 0.02. These results show that α-methoxystyrene acts as a chain transfer agent for methyl methacrylate and that the process produces polymers of lower molecular weight.

Example 66

Preparation of Ester-Terminated Low Molecular Weight Polymers of Styrene Using α-(4-Methoxycarbonylbenzyloxy)styrene (Formula II, $R^1$=phenyl, $R^2$=4-$CH_3OC(O)C_6H_4CH_2$—).

Samples of polystyrene prepared in the manner of example 48 using 0 mg, 132.1 mg, and 267.4 mg of α-(4-methoxycarbonylbenzyloxy)styrene had number-average molecular weights of 137000, 51580, and 31553, respectively. The chain transfer constant calculated from these data was 0.22. These results show that α-(4-methoxycarbonylbenzyloxy)styrene acts as a chain transfer agent for styrene and that the process produces polymers of lower molecular weight. A sample of polystyrene produced similarly using 745 mg of α-(4-methoxycarbonylbenzyloxy)styrene was precipitated two further times from ethyl acetate/methanol to remove traces of the unreacted chain transfer agent. The resulting polymer of number-average molecular weight 8298 had signals at δ 3.83 in the $^1$H NMR spectrum confirming the presence of the methyl ester group. Integration of the spectrum showed that one of these groups was present per polymer chain. The infrared spectrum of the polymer showed an absorption at 1720 $cm^{-1}$, also confirming the presence of an ester group. The polymer could be hydrolysed by methods well known to the art to give a polymer terminated at one end with a carboxylic acid group.

Example 67

Preparation of Ester-Terminated Low Molecular Weight Polymers of Methyl Methacrylate Using α-(4-Methoxycarbonylbenzyloxy)styrene (Formula II, $R^1$=phenyl, $R^2$=4-$CH_3OC(O)C_6H_4CH_2$—)

Samples of poly(methyl methacrylate) prepared in the manner of example 47 using 0 mg, 26.4 mg, and 44.1 mg of α-(4-methoxycarbonylbenzyloxy)styrene had number-average molecular weights of 246550, 24429, and 14955, respectively. The chain transfer constant calculated from these data was 0.70. These results show that α-(4-methoxycarbonylbenzyloxy)styrene acts as a chain transfer agent for methyl methacrylate and that the process produces ester-terminated polymers of low molecular weight.

Example 68

Preparation of Low Molecular Weight Hydroxy-Terminated Polymers of Methyl Methacrylate Using α-[4-(Hydroxymethyl)benzyloxy]styrene (Formula II, $R^1$=phenyl, $R^2$=$HOCH_2C_6H_4CH_2$—).

Samples of poly(methyl methacrylate) prepared in the manner of example 47 using 0 mg, 9.9 mg, 19.8 mg, and 39.9 mg of α-[4-(hydroxymethyl)benzyloxy]styrene had number-average molecular weights of 189492, 95120, 41752, and 20829, respectively. The chain transfer constant calculated from these data was 0.5. These results show that α-[4-(hydroxymethyl)benzyloxy]styrene acts as an efficient chain transfer agent for methyl methacrylate and that the process produces polymers of low molecular weight in a controlled manner. A sample of poly(methyl methacrylate) produced similarly using 436 mg of α-[4-(hydroxymethyl)benzyloxy]styrene was precipitated two further times from ethyl acetate/pentane to remove traces of the unreacted chain transfer agent. The resulting polymer of number-average molecular weight 1764 had signals at δ 4.52 in the $^1H$ NMR spectrum confirming the presence of a (hydroxymethyl)phenyl group. Integration of the spectrum showed that one of these groups was present per polymer chain.

Example 69

Preparation of Low Molecular Weight Hydroxy-Terminated Polymers of Styrene Using α-[4-(Hydroxymethyl)benzyloxy]styrene (Formula II, $R^1$=phenyl, $R^2$=$HOCH_2C_6H_4CH_2$—).

Samples of polystyrene prepared in the manner of example 48 using 0 mg, 20.1 mg, 40.1 mg, and 80.3 mg of α-[4-(hydroxymethyl)benzyloxy]styrene had number-average molecular weights of 112326, 76147, 56570, and 37926, respectively. The chain transfer constant calculated from these data was 0.24. These results show that α-[4-(hydroxymethyl)benzyloxy]styrene acts as an efficient chain transfer agent for styrene and that the process produces polymers of low molecular weight in a controlled manner. A sample of polystyrene produced similarly using 1.30 g of α-[4-(hydroxymethyl)benzyloxy]styrene was precipitated two further times from ethyl acetate/methanol to remove traces of the unreacted chain transfer agent. The resulting polymer of number-average molecular weight 10239 had signals at δ 4.50 in the $^1H$ NMR spectrum confirming the presence of a (hydroxymethyl)phenyl group. Integration of the spectrum showed that one of these groups was present per polymer chain.

Example 70

Preparation of Low Molecular Weight Hydroxy-Terminated Polymers of Methyl Acrylate Using α-[4-(Hydroxymethyl)benzyloxy]styrene (Formula II, $R^1$=phenyl, $R^2$=$HOCH_2C_6H_4CH_2$—).

Samples of poly(methyl acrylate) prepared in the manner of example 49 using 0 mg, 11.7 mg, and 25.3 mg of α-[4-(hydroxymethyl)benzyloxy]styrene had number-average molecular weights of 358538, 7064, and 3222, respectively. The chain transfer constant calculated from these data was 5.5. These results show that α-[4-(hydroxymethyl)benzyloxy]styrene acts as an efficient chain transfer agent for methyl acrylate and that the process produces polymers of low molecular weight in a controlled manner. A sample of poly(methyl acrylate) produced similarly using 41.6 mg of α-[4-(hydroxymethyl)benzyloxy]styrene was precipitated five further times from ethyl acetate/methanol and once from ethyl acetate/pentane at low temperature to remove traces of the unreacted chain transfer agent. The resulting polymer of number-average molecular weight 15548 had signals at δ 4.53 in the $^1H$ NMR spectrum confirming the presence of a (hydroxymethyl)phenyl group. Integration of the spectrum showed that one of these groups was present per polymer chain.

Example 71

Preparation of Low Molecular Weight Hydroxy-Terminated Polymers of Vinyl Acetate Using α-[4-(Hydroxymethyl)benzyloxy]styrene] (Formula II, $R^1$=phenyl, $R^2$=$HOCH_2C_6H_4CH_2$—).

Samples of poly(vinyl acetate) prepared in the manner of example 50 using 0 mg, 4.9 mg, 10.2 mg, and 20.0 mg of α-[4-(hydroxymethyl)benzyloxy]styrene had number-average molecular weights of 291871, 44164, 25185, and 11349, respectively. The chain transfer constant calculated from these data was 9.0. These results show that α-[4-(hydroxymethyl)benzyloxy]styrene acts as an efficient chain transfer agent for vinyl acetate and that the process produces hydroxy-terminated polymers of low molecular weight in a controlled manner.

Example 72

Preparation of Low Molecular Weight Nitrile-Terminated Polymers of Methyl Methacrylate Using α-(4-Cyanobenzyloxy)styrene (Formula II, $R^1$=phenyl, $R^2$=$NCC_6H_4CH_2$—).

Samples of poly(methyl methacrylate) prepared in the manner of example 47 using 0 mg, 10.0 mg, 21.8 mg, and 42.6 mg of α-(4-cyanobenzyloxy)styrene had number-average molecular weights of 242138, 46269, 26366, and 14551, respectively. The chain transfer constant calculated from these data was 0.77. These results show that α-(4-cyanobenzyloxy)styrene acts as an efficient chain transfer agent for methyl methacrylate and that the process produces nitrile-terminated polymers of low molecular weight in a controlled manner.

Example 73

Preparation of Low Molecular Weight Nitrile-Terminated Polymers of Styrene Using α-(4-Cyanobenyloxy)styrene (Formula II, $R^1$=phenyl, $R^2$=$NCC_6H_4CH_2$—).

Samples of polystyrene prepared in the manner of example 48 using 0 mg, 40.0 mg, and 81.0 mg of α-(4-cyanobenzyloxy)styrene had number-average molecular weights of 107520, 75745, and 58482, respectively.

The chain transfer constant calculated from these data was 0.21. These results show that α-(4-cyanobenzyloxy)styrene acts as an efficient chain transfer agent for styrene and that the process produces polymers of low molecular weight in a controlled manner. The infrared spectrum of the polymer showed an absorption at 2220 cm$^{-1}$ confirming the presence of a nitrile group.

Example 74

Preparation of Low Molecular Weight Methoxy-Terminated Polymers of Methyl Methacrylate Using α-(4-Methoxybenzyloxy)styrene (Formula II, $R^1$=phenyl, $R^2$=CH$_3$OC$_6$H$_4$CH$_2$—).

Samples of poly(methyl methacrylate) prepared in the manner of example 47 using 15.9 mg and 39.4 mg of α-(4-methoxybenzyloxy)styrene had number-average molecular weights of 37329 and 16096, respectively. The chain transfer constant calculated from these data was 0.66. These results show that α-(4-methoxybenzyloxy)styrene acts as an efficient chain transfer agent for methyl methacrylate and that the process produces methoxy-terminated polymers of low molecular weight in a controlled manner.

Example 75

Preparation of Low Molecular Weight Methoxy-Terminated Polymers of Styrene Using α-(4-Methoxybenzyloxy)styrene (Formula II, $R^1$=phenyl, $R^2$=CH$_3$OC$_6$H$_4$CH$_2$—).

Samples of polystyrene prepared in the manner of example 48 using 122.3 mg and 263.4 mg of α-(4-methoxybenzyloxy)styrene had number-average molecular weights of 56648 and 33395, respectively. The chain transfer constant calculated from these data was 0.19. These results show that α-(4-methoxybenzyloxy)styrene acts as an efficient chain transfer agent for styrene and that the process produces methoxy-terminated polymers of low molecular weight in a controlled manner.

Example 76

Preparation of Low Molecular Weight Amine-Terminated Polymers of Methyl Methacrylate Using α-[4-(Aminomethyl)benzyloxyl]styrene (Formula II, $R^1$=phenyl, $R^2$=H$_2$NCH$_2$C$_6$H$_4$CH$_2$—).

Samples of poly(methyl methacrylate) prepared in the manner of example 47 using 0 mg, 11.2 mg, 20.9 mg, and 39.8 mg of α-[4-(aminomethyl)benzyloxy]styrene had number-average molecular weights of 262866, 24717, 16088, and 7115, respectively. The chain transfer constant calculated from these data was 1.54. These results show that α-[4-(aminomethyl)benzyloxy]styrene acts as an efficient chain transfer agent for methyl methacrylate and that the process produces amine-terminated polymers of low molecular weight in a controlled manner.

Example 77

Preparation of Low Molecular Weight (Chloromethyl)phenyl-Terminated Polymers of Methyl Methacrylate Using a Mixture of α-Benzyloxy[4-(chloromethyl)styrene] and α-Benzyloxy[3-(chloromethyl)styrene] (Formula II, $R^1$=ClCH$_2$C$_6$H$_4$—, $R^2$=benzyl—).

Samples of poly(methyl methacrylate) prepared in the manner of example 47 using 0 mg, 25.3 mg, 44.1 mg, and 72.8 mg of α-benzyloxy[4-(chloromethyl)styrene] and α-benzyloxy[3-(chloromethyl)styrene] had number-average molecular weights of 246550, 35572, 23907, and 17418, respectively. The chain transfer constant calculated from these data was 0.44. These results show that α-benzyloxy[(chloromethyl)styrene] acts as an efficient chain transfer agent for methyl methacrylate and that the process produces polymers of low molecular weight in a controlled manner. A sample of poly(methyl methacrylate) produced. similarly using 300 mg of the chain transfer agent was precipitated two further times from ethyl acetate/pentane to remove traces of the unreacted chain transfer agent. The resulting polymer of number-average molecular weight 8034 had signals at δ 4.67 in the $^1$H NMR spectrum confirming the presence of a (chloromethyl)phenyl group. Polymers terminated with this benzylic chloride group react with a variety of nucleophiles to give products in which the chlorine atom is replaced by the nucleophile. For example, reaction with cyanate ion leads to polymers terminated with an isocyanate group.

Example 78

Preparation of Low Molecular Weight tert-Butyldimethylsilyloxy-Terminated Polymers of Methyl Methacrylate Using α-Benzyloxy[4-(tert-butyldimethylsilyloxymethyl)styrene] and α-Benzyloxy[3-(tert-butyldimethylsilyloxymethyl)styrene] (Formula II, $R^1$=(tert-butyldimethylsilyloxymethyl)phenyl, $R^2$=benzyl).

Samples of poly(methyl methacrylate) prepared in the manner of example 47 using 38.8 mg, 72.4 mg, and 117.3 mg of a mixture of α-benzyloxy[4-(tert-butyldimethylsilyloxymethyl)styrene] and α-benzyloxy[3-(tert-butyldimethylsilyloxymethyl)styrene] had number-average molecular weights of 27555, 13147 and 8436, respectively. The chain transfer constant calculated from these data was 0.66. These results show that the compounds act as efficient chain transfer agents for methyl methacrylate and that the process produces polymers of low molecular weight in a controlled manner. A sample of poly(methyl methacrylate) produced similarly using 392 mg of the mixture was precipitated two further times from ethyl acetate/pentane to remove traces of the unreacted chain transfer agent. The resulting polymer of number-average molecular weight 4414 had signals at δ 0.12 in the $^1$H NMR spectrum confirming the presence of the tert-butyldimethylsilyloxy group. Such a group can be readily converted by well-known methods (such as stirring with tetrabutylammonium fluoride in a solvent) to a hydroxyl group.

Example 79

Preparation of Low Molecular Weight Hydroxy-Terminated Polymers of Methyl Methacrylate Using α-Benzyloxy[4-(hydroxymethyl)styrene] and α-Benzyloxy[3-(hydroxymethyl)styrene] (Formula II, $R^1$=HOCH$_2$C$_6$H$_4$—, $R^2$=benzyl).

Samples of poly(methyl methacrylate) prepared in the manner of example 47 using 0 mg, 10.8 mg, and 20.1 mg of a mixture of α-benzyloxy[4-(hydroxymethyl)styrene] and α-benzyloxy[3-(hydroxymethyl)styrene] had number-average molecular weights of 182396, 110353, and 41759, respectively. The chain transfer constant calculated from these data was 0.41. These results show that the compounds act as efficient chain transfer agents for methyl methacrylate and that the process produces hydroxy-terminated polymers of low molecular weight. A sample of poly(methyl methacrylate) produced similarly using 345 mg of the mixture was precipitated two further times from ethyl acetate/pentane to remove traces of the unreacted chain transfer agent. The resulting polymer of number-average molecular weight 10975 had signals between δ 4.5 and 4.7 in the $^1$H NMR spectrum confirming the presence of a hydroxymethylphenyl group.

Example 80

Preparation of Low Molecular Weight Acetoxy-Terminated Polymers of Styrene Using α-Benzyloxy[4-(acetoxymethyl)styrene] and α-Benzyloxy[3-(acetoxymethyl)styrene] (Formula II, $R^1=CH_3CO_2CH_2C_6H_4-$, $R^2=$benzyl).

Samples of polystyrene prepared in the manner of example 48 using 100.2 mg, 151.6 mg, and 198.6 mg of a mixture of α-benzyloxy[4-(acetoxymethyl)styrene] and α-benzyloxy[3-(acetoxymethyl)styrene] had number-average molecular weights of 48465, 38481, and 31175, respectively. The chain transfer constant calculated from these data was 0.33. These results show that the mixture acts as an efficient chain transfer agent for styrene and that the process produces acetoxy-terminated polymers of low molecular weight in a controlled manner. A sample of polystyrene prepared similarly using 2 g of the mixture was precipitated two further times from ethyl acetate/methanol to remove traces of the unreacted chain transfer agent. The resulting polymer of number-average molecular weight 7673 had signals at δ 5.06 in the $^1$H NMR spectrum confirming the presence of an (acetoxymethyl)phenyl group. Integration of the spectrum showed that one of these groups was present per polymer chain. The infrared spectrum of the polymer showed an absorption at 1740 cm$^{-1}$ also confirming the presence of the ester group. This group could be readily hydrolysed to an OH group.

Example 81

Preparation of Low Molecular Weight Chlorophenyl-Terminated Polymers of Methyl Methacrylate Using α-Benzyloxy(4-chlorostyrene) (Formula II, $R^1=$4-chlorophenyl, $R^2=$benzyl)

Samples of poly(methyl methacrylate) prepared in the manner of example 47 using 22.8 mg and 49.1 mg of α-benzyloxy(4-chlorostyrene) had number-average molecular weights of 25000, and 11900 respectively. The chain transfer constant calculated from these data was 0.75. These results show that α-benzyloxy(4-chlorostyrene) acts as an efficient chain transfer agent for methyl methacrylate and that the process produces chlorophenyl-terminated polymers of low molecular weight in a controlled manner.

Example 82

Preparation of Low Molecular Weight Methoxy-Terminated Polymers of Methyl Methacrylate Using α-Benzyloxy(3-methoxystyrene) (Formula II, $R^1=$3-$CH_3OC_6H_4-$, $R^2=$benzyl).

Samples of poly(methyl methacrylate) prepared in the manner of example 47 using 24.8 mg and 40.2 mg of α-benzyloxy(3-methoxystyrene) had number-average molecular weights of 20423 and 12707, respectively. The chain transfer constant calculated from these data was 0.83. These results show that α-benzyloxy(3-methoxystyrene) acts as an efficient chain transfer agent for methyl methacrylate and that the process produces methoxy-terminated polymers of low molecular weight in a controlled manner.

Example 83

Preparation of Low Molecular Weight Methoxy-Terminated Polymers of Methyl Methacrylate Using α-Benzyloxy(4-methoxystyrene) (Formula II, $R^1=$4-$CH_3OC_6H_4-$, $R^2=$benzyl).

Samples of poly(methyl methacrylate) prepared in the manner of example 47 using 20.7 mg and 44.7 mg of α-benzyloxy(4-methoxystyrene) had number-average molecular weights of 38931 and 19947, respectively. The chain transfer constant calculated from these data was 0.46. These results show that α-benzyloxy(4-methoxystyrene) acts as an efficient chain transfer agent for methyl methacrylate and that the process produces methoxy-terminated polymers of low molecular weight in a controlled manner.

Example 84

Preparation of Low Molecular Weight α-Acetoxy, ω-Methoxy-carbonyl Polystyrene Using α-(4-Methoxycarbonylbenzyloxy)[4-(acetoxymethyl)styrene] and α-(4-Methoxycarbonylbenzyloxy)[3-(acetoxymethyl)styrene] (Formula II, $R^1=CH_3CO_2CH_2C_6H_4-$, $R^2=CH_3OC(O)CH_2C_6H_4CH_2-$).

Samples of polystyrene prepared in the manner of example 48 using 0 mg, 40.0 mg, 80.4 mg, and 160.0 mg of a mixture of α-(4-methoxycarbonylbenzyloxy) [4-(acetoxymethyl)styrene]and α-(4-methoxycarbonylbenzyloxy)[3-(acetoxymethyl)styrene] had number-average molecular weights of 120702, 97477, 78326, and 57711, respectively. The chain transfer constant calculated from these data was 0.18. These results show that the mixture acts as an efficient chain transfer agent for styrene and that the process produces bis-end-functional polymers of low molecular weight in a controlled manner. A sample of polystyrene produced similarly using 966 mg of che mixture was precipitated two further times from ethyl acetate/methanol to remove traces of the unreacted chain transfer agents. The resulting polymer of number-average molecular weight 10873 had signals at δ 3.82 and 5.05 in the $^1$H NMR spectrum confirming the presence of methyl ester groups and acetoxymethyl groups. Integration of the spectrum showed that one of each of these groups was present per polymer chain. The infrared spectrum of the polymer showed absorptions at 1720 and 1740 cm$^{-1}$ also confirming the presence of the ester groups. The resultant polymer could be readily hydrolysed by methods well known to the art to give a polymer terminated at one end with a hydroxyl group and terminated at the other end by a carboxylic acid moiety.

Example 85

Preparation of Low Molecular Weight α,ω-Dihydroxypoly(methyl methacrylate) Using α-[4-(Hydroxymethyl)benzyloxy][4-(hydroxymethyl)styrene] and α-[4-(Hydroxymethyl)benzyloxy][3-(hydroxymethyl)styrene] (Formula II, $R^1=HOCH_2C_6H_4-$, $R^2=HOCH_2C_6H_4CH_2-$).

Samples of poly(methyl methacrylate) prepared in the manner of example 47 using 0 mg, 10.1 mg, 18.9 mg, and 42.7 mg of a mixture of α-[4-(hydroxymethyl)benzyloxy][4-(hydroxymethyl)styrene] and α-[4-(hydroxymethyl)benzyloxy][3-(hydroxymethyl)styrene] had number-average molecular weights of 173410, 42227, 26264, and 15222, respectively. The chain transfer constant calculated from these data was 0.73. These results show that the compounds act as an efficient chain transfer agent for methyl methacrylate and that the process produces bis-hydroxy end-functional polymers of low molecular weight in a controlled manner. A sample of poly(methyl methacrylate) produced similarly using 374 mg of the mixture was precipitated one further time from ethyl acetate/pentane and three times from ethyl acetate/methanol remove traces of the unreacted chain transfer agent. The resulting polymer of number-average molecular weight 36422 had signals at δ4.5–4.7 in the $^1$H NMR spectrum confirming the presence of hydroxymethylphenyl groups. The infrared spectrum of the polymer showed a broad absorption at 3505 cm$^{-1}$ confirming the presence of the hydroxyl groups.

Example 86

Preparation of Low Molecular Weight α,ω-Dihydroxypolystyrene Using α-[4-(Hydroxymethyl)benzyloxy][4-(hydroxymethyl)styrene] and α-[4-(Hydroxymethyl)benzyloxy][3-(hydroxymethyl)styrene] (Formula II, R$^1$=HOCH$_2$C$_6$H$_4$—, R$^2$=HOCH$_2$C$_6$H$_4$CH$_2$—).

A sample of polystyrene produced in the manner of example 48 using 1.9 g of a mixture of α-[4-(hydroxymethyl)benzyloxy][4-(hydroxymethyl)styrene] and α-[4-(hydroxymethyl)benzyloxy][3-(hydroxymethyl)styrene] was precipitated three times from ethyl acetate/methanol to remove traces of the unreacted chain transfer agents. The resulting bis-end-functional polymer of number-average molecular weight 8942 had signals at δ 4.4–4.7 in the $^1$H NMR spectrum confirming the presence of hydroxymethylphenyl groups.

Example 87

Preparation of Low Molecular Weight α,ω-bis(t-Butyldimethylsilyloxymethyl)poly(methyl methacrylate) Using α-[4-(t-butyldimethylsilyloxymethyl)benzyloxy][4-(t-butyldimethylsilyloxymethyl)styrene] and α-[4-(t-butyldimethylsilyloxymethyl)benzyloxy][3-(t-butyldimethylsilyloxymethyl)styrene] (Formula II, R$^1$=(t-bytldimethylsilylxoymethyl)phenyl, R$^2$=4-(t-butyldimethylsilyloxymethyl)benzyl).

Samples of poly(methyl methacrylate) prepared in the manner of example 47 using 0 mg, 34.3 mg, 70.1 mg, and 97.5 mg of a mixture of α-[4-(t-butyldimethylsilyloxymethyl)benzyloxy][4-(t-butyldimethylsilyloxymethyl)styrene] and α-[4-(t-butyldimethylsilyloxymethyl)benzyloxy][3-(t-butyldimethylsilyloxymethyl)styrene] had number-average molecular weights of 227540, 32925, 18286, and 14520, respectively. The chain transfer constant calculated from these data was 0.65. These results show that these compounds act as an efficient chain transfer agent for methyl methacrylate and that the process produces bis-silyloxy end-functional polymers of low molecular weight in a controlled manner. A sample of poly(methyl methacrylate) produced similarly using 369 mg of the mixture was precipitated two further times from ethyl acetate/pentane to remove traces of the unreacted chain transfer agent. The resulting polymer of number-average molecular weight 5907 had signals at δ 0.0–0.14 and 4.6–4.8 in the $^1$H NMR spectrum confirming the presence of the t-butyldimethylsilyloxymethylphenyl groups. Integration of the spectrum showed that two of these groups were present per polymer chain.

Example 88

Preparation of Low Molecular Weight α-Hydroxy-, ω-Amino Poly(methyl methacrylate) Using α-[4-(Hydroxymethyl)benzyloxy][4-(aminomethyl)styrene] (Formula II, R$^1$=H$_2$NCH$_2$C$_6$H$_4$—, R$^2$=HOCH$_2$C$_6$H$_4$CH$_2$—).

Samples of poly(methyl methacrylate) prepared in the manner of example 47 using 0 mg, and 31.0 mg of α-[4-(hydroxymethyl)benzyloxy][4-(aminomethyl)styrene] had number-average molecular weights of 236538, and 24233, respectively. The chain transfer constant calculated from these data was 0.6. These results show that α-[4-(hydroxymethyl)benzyloxy][(aminomethyl)styrene] acts as an efficient chain transfer agent for methyl methacrylate and that the process produces polymers of low molecular weight terminated by an amino group and a hydroxyl group.

Example 89

Preparation of Low Molecular Weight Polyacrylonitrile Using α-Benzyloxystyrene (Formula II, R$^1$=phenyl, R$^2$=benzyl).

Azobisisobutyronitrile (7.4 mg) was dissolved in freshly distilled acrylonitrile (10 ml). An aliquot (2 ml) was removed and added to α-benzyloxystyrene (18.5 mg) and the mixture was polymerized in the absence of oxygen for 1 h at 60° C. The resulting polymer was precipitated in toluene. A portion (100 mg) of the dried polymer was dissolved in dimethylformamide (10 ml) and the viscosity was measured using a Gardiner Bubble viscometer. The resulting polymer had a viscosity less than that of tube B. A similar polymer prepared without added chain transfer agent had a viscosity equal to that of tube E. This result shows that the polymer prepared using α-benzyloxystyrene had a lower molecular weight than that prepared without, and that α-benzyloxystyrene acts as a chain transfer agent for acrylonitrile.

We claim:

1. An improved process for the production of polymers or oligomers of controllably reduced molecular weight by the free radical polymerization of monomers in the presence of an initiator and a chain transfer agent which is present in an effective amount to control the molecular weight thereof; wherein said chain transfer agent terminates the growth of the polymer chain by addition to the propagating polymer radical followed by expulsion of a radical which then initiates another polymer chain; wherein the improvement comprises the use of; a chain transfer agent selected from the group consisting of:

α-(carboxyalkanethiomethyl) acrylic acid;
alkyl α-(carboxyalkanethiomethyl) acrylate;
α-(t-butanethiomethyl) acrylonitrile;
ethyl α-(t-butanethiomethyl) acrylate
ethyl α-(trimethylsilylmethyl) acrylate;
ethyl α-(benzyenesulphonylmethyl) acrylate; and
ethyl α-(tri-n-butylstanylmethyl) acrylate.

2. The method of claim 1 wherein the chain transfer agent is ethyl α-(tri-n-butylstanylmethyl) acrylate.

3. The method of claim 1 wherein the chain transfer agent is α-(carboxyalkanethiomethyl) acrylic acid.

4. The method of claim 1 wherein the chain transfer agent is alkyl α-(carboxyalkanethiomethyl) acrylate.

5. The method of claim 4 wherein the chain transfer agent is ethyl α-(carboxyalkanethiomethyl) acrylate.

6. The method of claim 5 wherein the chain transfer agent is ethyl α-(carboxymethanethiomethyl) acrylate.

7. The method of claim 1 wherein the chain transfer agent is ethyl α-(t-butanethiomethyl) acrylate.

8. The method of claim 1 wherein the chain transfer agent is α-(t-butanethiomethyl) acrylonitrile.

9. The method of claim 1 wherein the chain transfer agent is ethyl α-(trimethylsilylmethyl) acrylate.

10. The method of claim 1 wherein the chain transfer agent is ethyl α-(benzyenesulphonylmethyl) acrylate.

11. The method of claim 3 wherein the chain transfer agent is α-(carboxymethanethiomethyl) acrylic acid.

12. An improved process for the production of polymers or oligomers of controlled molecular weight by the free radical polymerization of monomers in the presence of an initiator and a chain transfer agent which is present in an effective amount to control the molecular weight thereof; wherein said chain transfer agent terminates the growth of the polymer chain by addition to the propagating polymer radical followed by expulsion of a radical which then initiates another polymer chain; wherein the improvement comprises selecting a compound for use as the chain transfer agent; said compound having the formula:

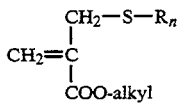

COO-alkyl wherein R is an alkyl, aryl, alkenyl or alkynyl group and n is 1.

13. An improved process for the production of polymers or oligomers of controlled molecular weight by the free radical polymerization of monomers in the presence of an initiator and a chain transfer agent which is present in an effective amount to control the molecular weight thereof; wherein said chain transfer agent terminates the growth of the polymer chain by addition to the propagating polymer radical followed by expulsion of a radical which then initiates another polymer chain; wherein the improvement comprises selecting a compound for use as the chain transfer agent; said compound having the formula:

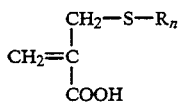

COOH wherein R is an alkyl, aryl, alkenyl or alkynyl group and n is 1.

14. An improved process for the production of polymers or oligomers of controlled molecular weight by the free radical polymerization of monomers in the presence of an initiator and a chain transfer agent which is present in an effective amount to control the molecular weight thereof; wherein said chain transfer agent terminates the growth of the polymer chain by addition to the propagating polymer radical followed by expulsion of a radical which then initiates another polymer chain; wherein the improvement comprises selecting a compound for use as the chain transfer agent; said compound having the formula:

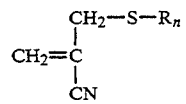

CN wherein R is an alkyl, aryl, alkenyl or alkynyl group and n is 1.

15. The method of claim 12 wherein said alkyl, aryl, alkenyl or alkynyl group includes a reactive substituent; said reactive substituent being selected so that it does not take part in the actual lowering of the molecular weight of said polymer or oligomer but is installed at the end of the polymer chain as said chain transfer agent terminates the growth of said polymer chain and said reactive substituent is capable of subsequent chemical reaction.

16. The method of claim 13 wherein said alkyl, aryl, alkenyl or alkynyl group includes a reactive substituent; said reactive substituent being selected so that it does not take part in the actual lowering of the molecular weight of said polymer or oligomer but is installed at the end of the polymer chain as said chain transfer agent terminates the growth of said polymer chain and said reactive substituent is capable of subsequent chemical reaction.

17. The method of claim 14 wherein said alkyl, aryl, alkenyl or alkynyl group includes a reactive substituent; said reactive substituent being selected so that it does not take part in the actual lowering of the molecular weight of said polymer or oligomer but is installed at the end of the polymer chain as said chain transfer agent terminates the growth of said polymer chain and said reactive substituent is capable of subsequent chemical reaction.

18. The method of claim 15 wherein said alkyl, aryl, alkenyl or alkynyl group includes a non-reactive substituent.

19. The nethod of claim 16 wherein said alkyl, aryl, alkenyl or alkynyl group includes a non-reactive substituent.

20. The method of claim 17 wherein said alkyl, aryl, alkenyl or alkynyl group includes a non-reactive substituent.

* * * * *